US011992363B2

(12) United States Patent
Sowards et al.

(10) Patent No.: US 11,992,363 B2
(45) Date of Patent: May 28, 2024

(54) DYNAMICALLY ADJUSTING ULTRASOUND-IMAGING SYSTEMS AND METHODS THEREOF

(71) Applicant: Bard Access Systems, Inc., Salt Lake City, UT (US)

(72) Inventors: Steffan Sowards, Salt Lake City, UT (US); William Robert McLaughlin, Bountiful, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 57 days.

(21) Appl. No.: 17/468,318

(22) Filed: Sep. 7, 2021

(65) Prior Publication Data

US 2022/0071589 A1  Mar. 10, 2022

Related U.S. Application Data

(60) Provisional application No. 63/075,707, filed on Sep. 8, 2020.

(51) Int. Cl.
*A61B 8/08* (2006.01)
*A61B 8/00* (2006.01)
*A61B 34/20* (2016.01)

(52) U.S. Cl.
CPC .......... *A61B 8/0841* (2013.01); *A61B 8/4494* (2013.01); *A61B 8/463* (2013.01);
(Continued)

(58) Field of Classification Search
CPC ... A61B 8/0841; A61B 8/0891; A61B 8/4461; A61B 2034/2051; A61B 8/4254;
(Continued)

(56) References Cited

U.S. PATENT DOCUMENTS 3,697,917 A 10/1972 Orth et al.
5,148,809 A 9/1992 Biegeleisen-Knight et al.
(Continued)

FOREIGN PATENT DOCUMENTS

CN 102871645 A 1/2013
CN 105107067 B 5/2018
(Continued)

OTHER PUBLICATIONS

Pagoulatos, N. et al. "New spatial localizer based on fiber optics with applications in 3D ultrasound imaging" Proceeding of Spie, vol. 3976 (Apr. 18, 2000; Apr. 18, 2000).
(Continued)

*Primary Examiner* — Colin T. Sakamoto
*Assistant Examiner* — Tommy T Ly
(74) *Attorney, Agent, or Firm* — Rutan & Tucker LLP

(57) ABSTRACT

Disclosed herein are dynamically adjusting ultrasound-imaging systems and methods thereof. For example, an ultrasound-imaging system can include an ultrasound probe, a console, and a display screen. The ultrasound probe includes an array of ultrasonic transducers that, when activated, emit generated ultrasound signals into a patient, receive reflected ultrasound signals from the patient, and convert the reflected ultrasound signals into corresponding electrical signals for processing into ultrasound images. The console is configured to execute instructions for dynamically adjusting a distance of activated ultrasonic transducers from a predefined target or area, an orientation of the activated ultrasonic transducers to the predefined target or area, or both the distance and the orientation of the activated ultrasonic transducers with respect to the predefined target or area. The display screen is configured to display a graphical user interface including the ultrasound images processed by the
(Continued)

console from the corresponding electrical signals of the ultrasound signals.

24 Claims, 11 Drawing Sheets

(52) U.S. Cl.
CPC ...... *A61B 34/20* (2016.02); *A61B 2034/2061* (2016.02); *A61B 2034/2063* (2016.02); *A61B 2562/0219* (2013.01); *A61B 2562/0223* (2013.01)

(58) Field of Classification Search
CPC ... A61B 8/4263; A61B 8/4488; A61B 8/4494; A61B 8/54; A61B 2562/0219; A61B 2562/0223; A61B 8/461; G01S 15/8925; G01S 15/8927
See application file for complete search history.

(56) References Cited

U.S. PATENT DOCUMENTS

| | | | |
|---|---|---|---|
| 5,181,513 A | 1/1993 | Touboul et al. | |
| 5,325,293 A | 6/1994 | Dorne | |
| 5,349,865 A | 9/1994 | Kavli et al. | |
| 5,441,052 A | 8/1995 | Miyajima | |
| 5,549,554 A | 8/1996 | Miraki | |
| 5,573,529 A | 11/1996 | Haak et al. | |
| 5,775,322 A | 7/1998 | Silverstein et al. | |
| 5,879,297 A | 3/1999 | Haynor et al. | |
| 5,897,503 A | 4/1999 | Lyon et al. | |
| 5,908,387 A | 6/1999 | LeFree et al. | |
| 5,967,984 A | 10/1999 | Chu et al. | |
| 5,970,119 A | 10/1999 | Hofmann | |
| 6,004,270 A | 12/1999 | Urbano et al. | |
| 6,019,724 A | 2/2000 | Gronningsaeter et al. | |
| 6,068,599 A | 5/2000 | Saito et al. | |
| 6,074,367 A | 6/2000 | Hubbell | |
| 6,129,668 A | 10/2000 | Haynor et al. | |
| 6,132,379 A | 10/2000 | Patacsil et al. | |
| 6,216,028 B1 | 4/2001 | Haynor et al. | |
| 6,233,476 B1 | 5/2001 | Strommer et al. | |
| 6,245,018 B1 | 6/2001 | Lee | |
| 6,263,230 B1 | 7/2001 | Haynor et al. | |
| 6,375,615 B1 | 4/2002 | Flaherty et al. | |
| 6,436,043 B2 | 8/2002 | Bonnefous | |
| 6,498,942 B1 | 12/2002 | Esenaliev et al. | |
| 6,503,205 B2 | 1/2003 | Manor et al. | |
| 6,508,769 B2 | 1/2003 | Bonnefous | |
| 6,511,458 B2 | 1/2003 | Milo et al. | |
| 6,524,249 B2 | 2/2003 | Moehring et al. | |
| 6,543,642 B1 | 4/2003 | Milliorn | |
| 6,554,771 B1 | 4/2003 | Buil et al. | |
| 6,592,520 B1 | 7/2003 | Peszynski et al. | |
| 6,592,565 B2 | 7/2003 | Twardowski | |
| 6,601,705 B2 | 8/2003 | Molina et al. | |
| 6,612,992 B1 | 9/2003 | Hossack et al. | |
| 6,613,002 B1 | 9/2003 | Clark et al. | |
| 6,623,431 B1 | 9/2003 | Sakuma et al. | |
| 6,641,538 B2 | 11/2003 | Nakaya et al. | |
| 6,647,135 B2 | 11/2003 | Bonnefous | |
| 6,687,386 B1 | 2/2004 | Ito et al. | |
| 6,733,458 B1* | 5/2004 | Steins | A61B 8/4254 600/461 |
| 6,749,569 B1 | 6/2004 | Pellegretti | |
| 6,754,608 B2 | 6/2004 | Svanerudh et al. | |
| 6,755,789 B2 | 6/2004 | Stringer et al. | |
| 6,840,379 B2 | 1/2005 | Franks-Farah et al. | |
| 6,857,196 B2 | 2/2005 | Dalrymple | |
| 6,979,294 B1 | 12/2005 | Selzer et al. | |
| 7,074,187 B2 | 7/2006 | Selzer et al. | |
| 7,244,234 B2 | 7/2007 | Ridley et al. | |
| 7,359,554 B2 | 4/2008 | Klingensmith et al. | |
| 7,534,209 B2 | 5/2009 | Abend et al. | |
| 7,599,730 B2 | 10/2009 | Hunter et al. | |
| 7,637,870 B2 | 12/2009 | Flaherty et al. | |
| 7,681,579 B2 | 3/2010 | Schwartz | |
| 7,691,061 B2 | 4/2010 | Hirota | |
| 7,699,779 B2 | 4/2010 | Sasaki et al. | |
| 7,720,520 B2 | 5/2010 | Willis | |
| 7,727,153 B2 | 6/2010 | Fritz et al. | |
| 7,734,326 B2 | 6/2010 | Pedain et al. | |
| 7,831,449 B2 | 11/2010 | Ying et al. | |
| 7,905,837 B2 | 3/2011 | Suzuki | |
| 7,925,327 B2 | 4/2011 | Weese | |
| 7,927,278 B2 | 4/2011 | Selzer et al. | |
| 8,014,848 B2 | 9/2011 | Birkenbach et al. | |
| 8,038,619 B2 | 10/2011 | Steinbacher | |
| 8,060,181 B2 | 11/2011 | Rodriguez Ponce et al. | |
| 8,075,488 B2 | 12/2011 | Burton | |
| 8,090,427 B2 | 1/2012 | Eck et al. | |
| 8,105,239 B2 | 1/2012 | Specht | |
| 8,172,754 B2 | 5/2012 | Watanabe et al. | |
| 8,175,368 B2 | 5/2012 | Sathyanarayana | |
| 8,200,313 B1 | 6/2012 | Rambod et al. | |
| 8,211,023 B2 | 7/2012 | Swan et al. | |
| 8,228,347 B2 | 7/2012 | Beasley et al. | |
| 8,298,147 B2 | 10/2012 | Huennekens et al. | |
| 8,303,505 B2 | 11/2012 | Webler et al. | |
| 8,323,202 B2 | 12/2012 | Roschak et al. | |
| 8,328,727 B2 | 12/2012 | Miele et al. | |
| 8,388,541 B2 | 3/2013 | Messerly et al. | |
| 8,409,103 B2 | 4/2013 | Grunwald et al. | |
| 8,449,465 B2 | 5/2013 | Nair et al. | |
| 8,553,954 B2 | 10/2013 | Saikia | |
| 8,556,815 B2 | 10/2013 | Pelissier et al. | |
| 8,585,600 B2 | 11/2013 | Liu et al. | |
| 8,622,913 B2 | 1/2014 | Dentinger et al. | |
| 8,706,457 B2 | 4/2014 | Hart et al. | |
| 8,727,988 B2 | 5/2014 | Flaherty et al. | |
| 8,734,357 B2 | 5/2014 | Taylor | |
| 8,744,211 B2 | 6/2014 | Owen | |
| 8,754,865 B2 | 6/2014 | Merritt et al. | |
| 8,764,663 B2 | 7/2014 | Smok et al. | |
| 8,781,194 B2 | 7/2014 | Malek et al. | |
| 8,781,555 B2 | 7/2014 | Burnside et al. | |
| 8,790,263 B2 | 7/2014 | Randall et al. | |
| 8,849,382 B2 | 9/2014 | Cox et al. | |
| 8,939,908 B2 | 1/2015 | Suzuki et al. | |
| 8,961,420 B2 | 2/2015 | Zhang | |
| 9,022,940 B2 | 5/2015 | Meier | |
| 9,138,290 B2 | 9/2015 | Hadjicostis | |
| 9,199,082 B1 | 12/2015 | Yared et al. | |
| 9,204,858 B2 | 12/2015 | Pelissier et al. | |
| 9,220,477 B2 | 12/2015 | Urabe et al. | |
| 9,295,447 B2 | 3/2016 | Shah | |
| 9,320,493 B2 | 4/2016 | Visveshwara | |
| 9,357,980 B2 | 6/2016 | Toji et al. | |
| 9,364,171 B2 | 6/2016 | Harris et al. | |
| 9,427,207 B2 | 8/2016 | Sheldon et al. | |
| 9,445,780 B2 | 9/2016 | Hossack et al. | |
| 9,456,766 B2 | 10/2016 | Cox et al. | |
| 9,456,804 B2 | 10/2016 | Tamada | |
| 9,468,413 B2 | 10/2016 | Hall et al. | |
| 9,492,097 B2 | 11/2016 | Wilkes et al. | |
| 9,521,961 B2 | 12/2016 | Silverstein et al. | |
| 9,554,716 B2 | 1/2017 | Burnside et al. | |
| 9,582,876 B2 | 2/2017 | Specht | |
| 9,610,061 B2 | 4/2017 | Ebbini et al. | |
| 9,636,031 B2 | 5/2017 | Cox | |
| 9,649,037 B2 | 5/2017 | Lowe et al. | |
| 9,649,048 B2 | 5/2017 | Cox et al. | |
| 9,702,969 B2 | 7/2017 | Hope Simpson et al. | |
| 9,715,757 B2 | 7/2017 | Ng et al. | |
| 9,717,415 B2 | 8/2017 | Cohen et al. | |
| 9,731,066 B2 | 8/2017 | Liu et al. | |
| 9,814,433 B2 | 11/2017 | Benishti et al. | |
| 9,814,531 B2 | 11/2017 | Yagi et al. | |
| 9,861,337 B2 | 1/2018 | Patwardhan et al. | |
| 9,895,138 B2 | 2/2018 | Sasaki | |
| 9,913,605 B2 | 3/2018 | Harris et al. | |
| 9,949,720 B2 | 4/2018 | Southard et al. | |
| 10,043,272 B2 | 8/2018 | Forzoni et al. | |

(56) References Cited

U.S. PATENT DOCUMENTS

| | | |
|---|---|---|
| 10,449,330 B2 | 10/2019 | Newman et al. |
| 10,524,691 B2 | 1/2020 | Newman et al. |
| 10,751,509 B2 | 8/2020 | Misener |
| 11,564,861 B1 | 1/2023 | Gaines |
| 2002/0038088 A1 | 3/2002 | Imran et al. |
| 2003/0047126 A1 | 3/2003 | Tomaschko |
| 2003/0106825 A1 | 6/2003 | Molina et al. |
| 2003/0120154 A1 | 6/2003 | Sauer et al. |
| 2003/0135115 A1 | 7/2003 | Burdette et al. |
| 2003/0149366 A1 | 8/2003 | Stringer et al. |
| 2004/0015080 A1 | 1/2004 | Kelly et al. |
| 2004/0055925 A1 | 3/2004 | Franks-Farah et al. |
| 2004/0197267 A1 | 10/2004 | Black et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0004290 A1 | 1/2006 | Smith et al. |
| 2006/0013523 A1 | 1/2006 | Childlers et al. |
| 2006/0015039 A1 | 1/2006 | Cassidy et al. |
| 2006/0020204 A1 | 1/2006 | Serra et al. |
| 2006/0047617 A1 | 3/2006 | Bacioiu et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0167738 A1 | 7/2007 | Timinger et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2007/0287886 A1 | 12/2007 | Saadat |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0108930 A1 | 5/2008 | Weitzel et al. |
| 2008/0125651 A1 | 5/2008 | Watanabe et al. |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0012401 A1 | 1/2009 | Steinbacher |
| 2009/0074280 A1 | 3/2009 | Lu et al. |
| 2009/0124903 A1 | 5/2009 | Osaka |
| 2009/0137887 A1 | 5/2009 | Shariati et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0281413 A1 | 11/2009 | Boyden et al. |
| 2009/0306509 A1 | 12/2009 | Pedersen et al. |
| 2010/0010348 A1 | 1/2010 | Halmann |
| 2010/0211026 A2 | 8/2010 | Sheetz et al. |
| 2010/0249598 A1 | 9/2010 | Smith et al. |
| 2010/0286515 A1 | 11/2010 | Gravenstein et al. |
| 2010/0312121 A1 | 12/2010 | Guan |
| 2010/0324423 A1 | 12/2010 | El-Aklouk et al. |
| 2011/0002518 A1 | 1/2011 | Ziv-Ari et al. |
| 2011/0026796 A1 | 2/2011 | Hyun et al. |
| 2011/0071404 A1 | 3/2011 | Schmitt et al. |
| 2011/0074244 A1 | 3/2011 | Osawa |
| 2011/0087107 A1 | 4/2011 | Lindekugel et al. |
| 2011/0166451 A1 | 7/2011 | Blaivas et al. |
| 2011/0282188 A1 | 11/2011 | Burnside et al. |
| 2011/0295108 A1 | 12/2011 | Cox et al. |
| 2011/0313293 A1 | 12/2011 | Lindekugel et al. |
| 2012/0165679 A1 | 6/2012 | Orome et al. |
| 2012/0179038 A1 | 7/2012 | Meurer et al. |
| 2012/0179042 A1 | 7/2012 | Fukumoto et al. |
| 2012/0179044 A1 | 7/2012 | Chiang et al. |
| 2012/0197132 A1 | 8/2012 | O'Connor |
| 2012/0220865 A1 | 8/2012 | Brown et al. |
| 2012/0277576 A1 | 11/2012 | Lui |
| 2013/0041250 A1 | 2/2013 | Pelissier et al. |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0197367 A1 | 8/2013 | Smok et al. |
| 2013/0218024 A1 | 8/2013 | Boctor et al. |
| 2013/0323700 A1 | 12/2013 | Samosky et al. |
| 2013/0338503 A1 | 12/2013 | Cohen et al. |
| 2013/0338508 A1 | 12/2013 | Nakamura et al. |
| 2014/0005530 A1 | 1/2014 | Liu et al. |
| 2014/0031694 A1 | 1/2014 | Solek |
| 2014/0066779 A1 | 3/2014 | Nakanishi |
| 2014/0073976 A1 | 3/2014 | Fonte et al. |
| 2014/0100440 A1 | 4/2014 | Cheline et al. |
| 2014/0114194 A1 | 4/2014 | Kanayama et al. |
| 2014/0180098 A1 | 6/2014 | Flaherty et al. |
| 2014/0180116 A1 | 6/2014 | Lindekugel et al. |
| 2014/0188133 A1 | 7/2014 | Misener |
| 2014/0188440 A1 | 7/2014 | Donhowe et al. |
| 2014/0276059 A1 | 9/2014 | Sheehan |
| 2014/0276069 A1 | 9/2014 | Amble et al. |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2014/0357994 A1 | 12/2014 | Jin et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0209113 A1 | 7/2015 | Burkholz et al. |
| 2015/0209510 A1 | 7/2015 | Burkholz et al. |
| 2015/0209526 A1 | 7/2015 | Matsubara et al. |
| 2015/0297097 A1 | 10/2015 | Matsubara et al. |
| 2015/0359520 A1 | 12/2015 | Shan et al. |
| 2015/0359991 A1 | 12/2015 | Dunbar et al. |
| 2016/0000367 A1 | 1/2016 | Lyon |
| 2016/0029995 A1 | 2/2016 | Navratil et al. |
| 2016/0113699 A1 | 4/2016 | Sverdlik et al. |
| 2016/0120607 A1 | 5/2016 | Sorotzkin et al. |
| 2016/0157831 A1 | 6/2016 | Kang et al. |
| 2016/0166232 A1 | 6/2016 | Merritt |
| 2016/0202053 A1 | 7/2016 | Walker et al. |
| 2016/0213398 A1 | 7/2016 | Liu |
| 2016/0259992 A1 | 9/2016 | Knodt et al. |
| 2016/0278869 A1 | 9/2016 | Grunwald |
| 2016/0296208 A1 | 10/2016 | Sethuraman et al. |
| 2016/0374616 A1 | 12/2016 | Mauldin, Jr. et al. |
| 2017/0020561 A1* | 1/2017 | Cox ................ A61M 25/0108 |
| 2017/0079548 A1 | 3/2017 | Silverstein et al. |
| 2017/0143312 A1 | 5/2017 | Hedlund et al. |
| 2017/0164923 A1 | 6/2017 | Matsumoto |
| 2017/0172666 A1 | 6/2017 | Govari et al. |
| 2017/0215842 A1 | 8/2017 | Ryu et al. |
| 2017/0252004 A1 | 9/2017 | Broad et al. |
| 2017/0328751 A1 | 11/2017 | Lemke |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0228465 A1 | 8/2018 | Southard et al. |
| 2018/0235709 A1* | 8/2018 | Donhowe ................ G06T 7/33 |
| 2018/0289927 A1 | 10/2018 | Messerly |
| 2018/0296185 A1* | 10/2018 | Cox ................ A61B 8/0841 |
| 2018/0310955 A1 | 11/2018 | Lindekugel et al. |
| 2018/0344293 A1 | 12/2018 | Raju et al. |
| 2019/0060001 A1 | 2/2019 | Kohli et al. |
| 2019/0060014 A1 | 2/2019 | Hazelton et al. |
| 2019/0125210 A1 | 5/2019 | Govari et al. |
| 2019/0200951 A1* | 7/2019 | Meier ................ A61B 8/54 |
| 2019/0239848 A1 | 8/2019 | Bedi et al. |

(56) References Cited

U.S. PATENT DOCUMENTS

| | | |
|---|---|---|
| 2019/0307419 A1 | 10/2019 | Durfee |
| 2019/0307515 A1* | 10/2019 | Naito .................. A61B 34/20 |
| 2019/0365347 A1 | 12/2019 | Abe |
| 2019/0365348 A1* | 12/2019 | Toume ................. A61B 8/065 |
| 2020/0069929 A1 | 3/2020 | Mason et al. |
| 2020/0113540 A1 | 4/2020 | Gijsbers et al. |
| 2020/0163654 A1 | 5/2020 | Satir et al. |
| 2020/0200900 A1 | 6/2020 | Asami et al. |
| 2020/0230391 A1 | 7/2020 | Burkholz et al. |
| 2020/0281563 A1 | 9/2020 | Muller et al. |
| 2020/0359990 A1 | 11/2020 | Poland et al. |
| 2021/0059639 A1 | 3/2021 | Howell |
| 2021/0137492 A1 | 5/2021 | Imai |
| 2021/0161510 A1 | 6/2021 | Sasaki et al. |
| 2021/0186467 A1 | 6/2021 | Urabe et al. |
| 2021/0267570 A1 | 9/2021 | Ulman et al. |
| 2021/0315538 A1 | 10/2021 | Brandl et al. |
| 2022/0039777 A1 | 2/2022 | Durfee |
| 2022/0039829 A1 | 2/2022 | Zijlstra et al. |
| 2022/0096797 A1 | 3/2022 | Prince |
| 2022/0104791 A1 | 4/2022 | Matsumoto |
| 2022/0104886 A1 | 4/2022 | Blanchard et al. |
| 2022/0117582 A1 | 4/2022 | McLaughlin et al. |
| 2022/0160434 A1 | 5/2022 | Messerly et al. |
| 2022/0168050 A1 | 6/2022 | Sowards et al. |
| 2022/0172354 A1 | 6/2022 | Misener et al. |
| 2022/0330922 A1 | 10/2022 | Sowards et al. |
| 2022/0334251 A1 | 10/2022 | Sowards et al. |
| 2023/0107629 A1 | 4/2023 | Sowards et al. |
| 2023/0132148 A1 | 4/2023 | Sowards et al. |
| 2023/0135562 A1 | 5/2023 | Misener et al. |
| 2023/0138970 A1 | 5/2023 | Sowards et al. |
| 2023/0148872 A1 | 5/2023 | Sowards et al. |
| 2023/0201539 A1 | 6/2023 | Howell |
| 2023/0277153 A1 | 9/2023 | Sowards et al. |
| 2023/0277154 A1 | 9/2023 | Sowards et al. |
| 2023/0293143 A1 | 9/2023 | Sowards et al. |
| 2023/0397900 A1 | 12/2023 | Prince |

FOREIGN PATENT DOCUMENTS

| | | |
|---|---|---|
| EP | 0933063 A1 | 8/1999 |
| EP | 1504713 A1 | 2/2005 |
| EP | 1591074 B1 | 5/2008 |
| EP | 2823766 A1 | 1/2015 |
| EP | 3181083 A1 | 6/2017 |
| EP | 3870059 | 9/2021 |
| JP | 2000271136 A | 10/2000 |
| JP | 2007222291 A | 9/2007 |
| JP | 2014150928 A | 8/2014 |
| JP | 2018175547 A | 11/2018 |
| KR | 20180070878 A | 6/2018 |
| KR | 102176196 B1 | 11/2020 |
| WO | 2010029521 A2 | 3/2010 |
| WO | 2010076808 A1 | 7/2010 |
| WO | 2013059714 A1 | 4/2013 |
| WO | 2014/115150 A1 | 7/2014 |
| WO | 2015/017270 A1 | 2/2015 |
| WO | 2016/081023 A1 | 5/2016 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020067897 A1 | 4/2020 |
| WO | 2020083660 A1 | 4/2020 |
| WO | 2020/186198 A1 | 9/2020 |
| WO | WO-2021198226 A1 * | 10/2021 |
| WO | 2022/072727 A2 | 4/2022 |
| WO | 2022/081904 A1 | 4/2022 |
| WO | 2022/119853 A1 | 6/2022 |
| WO | 2022115479 A1 | 6/2022 |
| WO | 2022119856 A1 | 6/2022 |
| WO | 2022/221703 A1 | 10/2022 |
| WO | 2022/221714 A1 | 10/2022 |
| WO | 2023059512 A1 | 4/2023 |
| WO | 2023076268 A1 | 5/2023 |
| WO | 2023081220 A1 | 5/2023 |
| WO | 2023081223 A1 | 5/2023 |
| WO | 2023091424 A1 | 5/2023 |

OTHER PUBLICATIONS

U.S. Appl. No. 17/020,476, filed Sep. 14, 2020 Final Office Action dated Jun. 9, 2022.

PCT/US2022/025082 filed Apr. 15, 2022 International Search Report and Written Opinion dated Jul. 11, 2022.

PCT/US2022/025097 filed Apr. 15, 2022 International Search Report and Written Opinion dated Jul. 8, 2022.

U.S. Appl. No. 17/020,476, filed Sep. 14, 2020 Advisory Action dated Aug. 19, 2022.

U.S. Appl. No. 17/020,476, filed Sep. 14, 2020 Non-Final Office Action dated Sep. 23, 2022.

U.S. Appl. No. 17/471,015, filed Sep. 9, 2021 Non-Final Office Action dated Aug. 16, 2022.

Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).

PCT/US2021/045218 filed Aug. 9, 2021 International Search Report and Written Opinion dated Nov. 23, 2021.

PCT/US2021/049123 filed Sep. 3, 2021 International Search Report and Written Opinion dated Feb. 4, 2022.

PCT/US2021/060622 filed Nov. 23, 2021 International Search Report and Written Opinion dated Mar. 3, 2022.

PCT/US2021/061267 filed Nov. 30, 2021 International Search Report and Written Opinion dated Mar. 9, 2022.

PCT/US2021/061276 filed Nov. 30, 2021 International Search Report and Written Opinion dated Mar. 9, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.

U.S. Appl. No. 15/951,903, filed Apr. 12, 2018 Board Decision dated Apr. 20, 2022.

U.S. Appl. No. 15/951,903, filed Apr. 12, 2018 Notice of Allowance dated May 2, 2022.

William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

PCT/US2022/048716 filed Nov. 2, 2022 International Search Report and Written Opinion dated Feb. 24, 2023.

PCT/US2022/048722 filed Nov. 2, 2022 International Search Report and Written Opinion dated Feb. 24, 2023.

PCT/US2022047727 filed Oct. 25, 2022 International Search Report and Written Opinion dated Jan. 25, 2023.

U.S. Appl. No. 17/020,476, filed Sep. 14, 2020 Final Office Action dated Jan. 5, 2023.

U.S. Appl. No. 17/471,015, filed Sep. 9, 2021 Non-Final Office Action dated Mar. 30, 2023.

U.S. Appl. No. 17/538,911, filed Nov. 30, 2021 Non-Final Office Action dated Mar. 2, 2023.

PCT/US12/61182 International Seach Report and Written Opinion dated Mar. 11, 2013.

PCT/US2021/049294 filed Sep. 7, 2021 International Search Report and Written Opinion dated Dec. 8, 2021.

PCT/US2021/049712 filed Sep. 9, 2021 International Search Report and Written Opinion dated Dec. 14, 2021.

PCT/US2021/052055 filed Sep. 24, 2021 International Search Report and Written Opinion dated Dec. 20, 2021.

(56) References Cited

OTHER PUBLICATIONS

U.S. Appl. No. 13/656,563, filed Oct. 19, 2012 Decision on Appeal dated Nov. 1, 2017.
U.S. Appl. No. 13/656,563, filed Oct. 19, 2012 Examiner's Answer dated Nov. 16, 2015.
U.S. Appl. No. 13/656,563, filed Oct. 19, 2012 Final Office Action dated Dec. 5, 2014.
U.S. Appl. No. 13/656,563, filed Oct. 19, 2012 Non-Final Office Action dated Jul. 18, 2014.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 15/951,903, filed Apr. 12, 2018 Advisory Action dated Dec. 22, 2020.
U.S. Appl. No. 15/951,903, filed Apr. 12, 2018 Examiner's Answer dated Jun. 3, 2021.
U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.
U.S. Appl. No. 17/020,476, filed Sep. 14, 2020 Non-Final Office Action dated Feb. 9, 2022.
PCT/US2022/049983 filed Nov. 15, 2022 International Search Report and Written Opinion dated Mar. 29, 2023.
PCT/US2023/014143 filed Feb. 28, 2023 International Search Report and Written Opinion dated Jun. 12, 2023.
PCT/US2023/015266 filed Mar. 15, 2023 International Search Report and Written Opinion dated May 25, 2023.
Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.
U.S. Appl. No. 17/020,476, filed Sep. 14, 2020 Notice of Allowance dated Apr. 28, 2022.
U.S. Appl. No. 17/534,099, filed Nov. 23, 2021 Non-Final Office Action dated Mar. 31, 2023.
U.S. Appl. No. 17/684,180, filed Mar. 1, 2022 Restriction Requirement dated May 19, 2023.
EP 20866520.8 filed Apr. 5, 2022 Extended European Search Report dated Aug. 22, 2023.
U.S. Appl. No. 17/471,015, filed Sep. 9, 2021 Final Office Action dated Oct. 12, 2023.
U.S. Appl. No. 17/534,099, filed Nov. 23, 2021 Final Office Action dated Sep. 29, 2023.
U.S. Appl. No. 17/538,911, filed Nov. 30, 2021 Final Office Action dated Sep. 13, 2023.
U.S. Appl. No. 17/684,180, filed Mar. 1, 2022 Non-Final Office Action dated Jul. 28, 2023.
U.S. Appl. No. 17/722,151, filed Apr. 15, 2022 Non-Final Office Action dated Sep. 7, 2023.
PCT/US2022/025097 filed Apr. 15, 2021 International Preliminary Report on Patentability dated Oct. 26, 2023.
PCT/US2023/030970 filed Aug. 23, 2023 International Search Report and Written Opinion dated Oct. 30, 2023.
U.S. Appl. No. 17/538,911, filed Nov. 30, 2021 Advisory Action dated Nov. 22, 2023.
U.S. Appl. No. 17/722,151, filed Apr. 15, 2022 Final Office Action dated Nov. 6, 2023.
U.S. Appl. No. 17/894,460, filed Aug. 24, 2022 Non-Final Office Action dated Nov. 6, 2023.
U.S. Appl. No. 17/471,015, filed Sep. 9, 2021 Advisory Action dated Feb. 2, 2024.
U.S. Appl. No. 17/534,099, filed Nov. 23, 2021 Advisory Action dated Dec. 8, 2023.
U.S. Appl. No. 17/538,943, filed Nov. 30, 2021 Non-Final Office Action dated Jan. 30, 2024.
U.S. Appl. No. 17/684,180, filed Mar. 1, 2022 Final Office Action dated Jan. 18, 2024.
U.S. Appl. No. 17/722,111, filed Apr. 15, 2022 Non-Final Office Action dated Dec. 22, 2023.
U.S. Appl. No. 17/722,151, filed Apr. 15, 2022 Advisory Action dated Jan. 2, 2024.
U.S. Appl. No. 17/894,460, filed Aug. 24, 2022 Final Office Action dated Jan. 31, 2024.

* cited by examiner

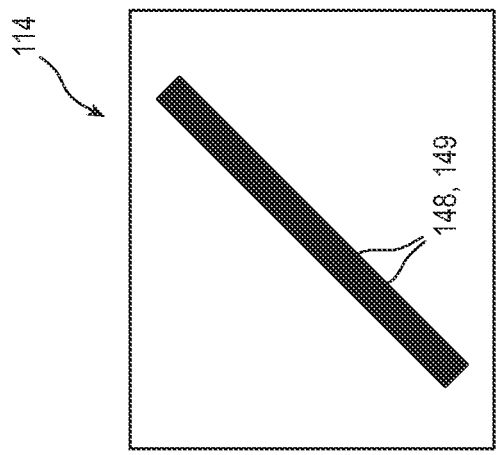
*FIG. 22*
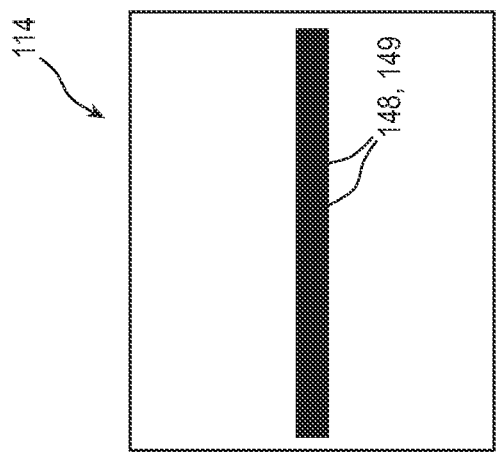
*FIG. 21*
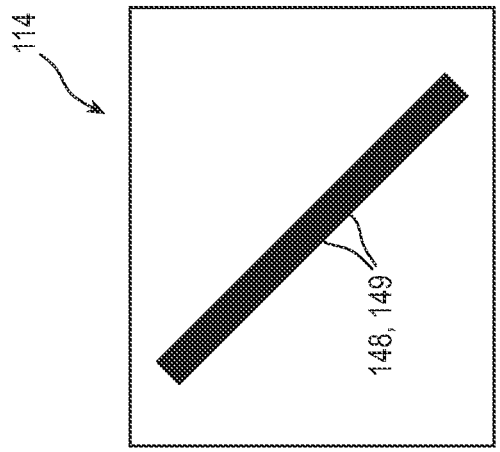
*FIG. 23*
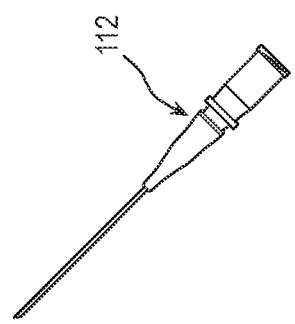
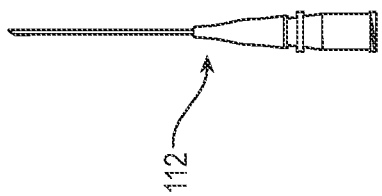
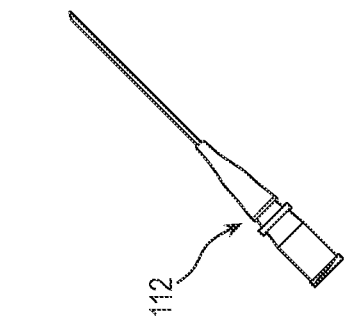

DYNAMICALLY ADJUSTING ULTRASOUND-IMAGING SYSTEMS AND METHODS THEREOF

PRIORITY

This application claims the benefit of priority to U.S. Provisional Patent Application No. 63/075,707, filed Sep. 8, 2020, which is incorporated by reference in its entirety into this application.

BACKGROUND

Ultrasound imaging is a widely accepted tool for guiding interventional instruments such as needles to targets such as blood vessels or organs in the human body. In order to successfully guide, for example, a needle to a blood vessel using ultrasound imaging, the needle is monitored in real-time both immediately before and after a percutaneous puncture in order to enable a clinician to determine the distance and the orientation of the needle to the blood vessel and ensure successful access thereto. However, through inadvertent movement of an ultrasound probe during the ultrasound imaging, the clinician can lose both the blood vessel and the needle, which can be difficult and time consuming to find again. In addition, it is often easier to monitor the distance and orientation of the needle immediately before the percutaneous puncture with a needle plane including the needle perpendicular to an image plane of the ultrasound probe. And it is often easier to monitor the distance and orientation of the needle immediately after the percutaneous puncture with the needle plane parallel to the image plane. As with inadvertently moving the ultrasound probe, the clinician can lose both the blood vessel and the needle when adjusting the image plane before and after the percutaneous puncture, which can be difficult and time consuming to find again. What is needed are ultrasound-imaging systems and methods thereof that can dynamically adjust the image plane to facilitate guiding interventional instruments to targets in at least the human body.

Disclosed herein are dynamically adjusting ultrasound-imaging systems and methods thereof.

SUMMARY

Disclosed herein is an ultrasound-imaging system including, in some embodiments, an ultrasound probe, a console, and a display screen. The ultrasound probe includes an array of ultrasonic transducers. Activated ultrasonic transducers of the array of ultrasonic transducers are configured to emit generated ultrasound signals into a patient, receive reflected ultrasound signals from the patient, and convert the reflected ultrasound signals into corresponding electrical signals of the ultrasound signals for processing into ultrasound images. The console is configured to communicate with the ultrasound probe. The console includes memory with executable instructions and a processor configured to execute the instructions. The instructions are for dynamically adjusting a distance of the activated ultrasonic transducers from a predefined target or area, an orientation of the activated ultrasonic transducers to the predefined target or area, or both the distance and the orientation of the activated ultrasonic transducers with respect to the predefined target or area. The instructions are also for processing the corresponding electrical signals of the ultrasound signals into the ultrasound images. The display screen is configured to communicate with the console. The display screen is configured to display a graphical user interface ("GUI") including the ultrasound images.

In some embodiments, the ultrasound probe further includes an array of magnetic sensors. The magnetic sensors are configured to convert magnetic signals from a magnetized medical device into corresponding electrical signals of the magnetic signals. The electrical signals are processed by the console into distance and orientation information with respect to the predefined target or area for display of an iconographic representation of the medical device on the display screen.

In some embodiments, the distance and orientation of the activated ultrasonic transducers is adjusted with respect to the predefined target or area when the medical device is brought into proximity of the ultrasound probe. An image plane is established by the activated ultrasonic transducers being perpendicular or parallel to a medical-device plane including the medical device for accessing the predefined target or area with the medical device.

In some embodiments, the distance and orientation of the activated ultrasonic transducers is adjusted with respect to a blood vessel as the predefined target. An image plane is established by the activated ultrasonic transducers being perpendicular or parallel to the blood vessel in accordance with an orientation of the blood vessel.

In some embodiments, the ultrasound-imaging system further includes a stand-alone optical interrogator communicatively coupled to the console or an integrated optical interrogator integrated into the console, as well as an optical-fiber stylet. The optical interrogator is configured to emit input optical signals, receive reflected optical signals, and convert the reflected optical signals into corresponding electrical signals of the optical signals for processing by the console into distance and orientation information with respect to the predefined target or area for display of an iconographic representation of a medical device on the display. The optical-fiber stylet configured to be disposed in a lumen of the medical device. The optical-fiber stylet is configured to convey the input optical signals from the optical interrogator to a number of fiber Bragg grating ("FBG") sensors along a length of the optical-fiber stylet. The optical-fiber stylet is also configured to convey the reflected optical signals from the number of FBG sensors back to the optical interrogator.

In some embodiments, the distance and orientation of the activated ultrasonic transducers is adjusted with respect to the predefined target or area when the medical device is brought into proximity of the ultrasound probe. An image plane is established by the activated ultrasonic transducers being perpendicular or parallel to a medical-device plane including the medical device for accessing the predefined target or area with the medical device.

In some embodiments, the distance and orientation of the activated ultrasonic transducers is adjusted with respect to a blood vessel as the predefined target. An image plane is established by the activated ultrasonic transducers being perpendicular or parallel to the blood vessel in accordance with an orientation of the blood vessel.

In some embodiments, the image plane includes a blood vessel as the predefined target or area and the medical device includes a needle, the image plane being perpendicular to the medical-device plane upon approach of the needle and parallel to the medical-device plane upon a percutaneous puncture with the needle.

In some embodiments, the array of ultrasonic transducers is a two-dimensional ("2-D") array of ultrasonic transducers.

The activated ultrasonic transducers are an approximately linear subset of ultrasonic transducers of the 2-D array of ultrasonic transducers activated by the console at any given time.

In some embodiments, the array of ultrasonic transducers is a movable linear array of ultrasonic transducers. The activated ultrasonic transducers are a subset of the ultrasonic transducers up to all the ultrasonic transducers in the linear array of ultrasonic transducers activated by the console at any given time.

In some embodiments, the ultrasound probe further includes an accelerometer, a gyroscope, a magnetometer, or a combination thereof configured to provide positional-tracking data to the console. The processor is further configured to execute the instructions for processing the positional-tracking data for the adjusting of the distance of the activated ultrasonic transducers from the predefined target or area, the orientation of the activated ultrasonic transducers to the predefined target or area, or both the distance and the orientation of the activated ultrasonic transducers with respect to the predefined target or area.

In some embodiments, the distance and the orientation of the activated ultrasonic transducers is maintained with respect to the predefined target or area when the ultrasound probe is inadvertently moved with respect to the predefined target or area.

Also disclosed herein is a method of an ultrasound-imaging system including a non-transitory computer-readable medium ("CRM") having executable instructions that cause the ultrasound-imaging system to perform a set of operations for ultrasound imaging when the instructions are executed by a processor of a console of the ultrasound-imaging system. The method includes, in some embodiments, an activating operation, an adjusting operation, a first processing operation, and a first displaying operation. The activating operation includes activating ultrasonic transducers of an array of ultrasonic transducers of an ultrasound probe communicatively coupled to the console. With the activating operation, the ultrasonic transducers emit generated ultrasound signals into a patient, receive reflected ultrasound signals from the patient, and convert the reflected ultrasound signals into corresponding electrical signals of the ultrasound signals for processing into ultrasound images. The adjusting operation includes dynamically adjusting a distance of activated ultrasonic transducers from a predefined target or area, an orientation of the activated ultrasonic transducers to the predefined target or area, or both the distance and the orientation of the activated ultrasonic transducers with respect to the predefined target or area. The first processing operation includes processing the corresponding electrical signals of the ultrasound signals into the ultrasound images. The first displaying operation includes displaying on a display screen communicatively coupled to the console a GUI including the ultrasound images.

In some embodiments, the method further includes a converting operation, a second processing operation, and a second displaying operation. The converting operation includes converting magnetic signals from a magnetized medical device with an array of magnetic sensors of the ultrasound probe into corresponding electrical signals of the magnetic signals. The second processing operation includes processing the corresponding electrical signals of the magnetic signals with the processor into distance and orientation information with respect to the predefined target or area. The second displaying operation includes displaying an iconographic representation of the medical device on the display screen.

In some embodiments, the method further includes an adjusting operation in response to the magnetic signals. The adjusting operation includes adjusting the distance and orientation of the activated ultrasonic transducers with respect to the predefined target or area when the medical device is brought into proximity of the ultrasound probe. The adjusting operation establishes an image plane by the activated ultrasonic transducers perpendicular or parallel to a medical-device plane including the medical device for accessing the predefined target or area with the medical device.

In some embodiments, the method further includes an adjusting operation in response to an orientation of a blood vessel as the predefined target. The adjusting operation includes adjusting the distance and orientation of the activated ultrasonic transducers with respect to the orientation of the blood vessel. The adjusting operation establishes an image plane by the activated ultrasonic transducers perpendicular or parallel to the blood vessel.

In some embodiments, the method further include optical signal-related operations, as well as a third processing operation and a third displaying operation. The optical signal-related operations include emitting input optical signals, receiving reflected optical signals, and converting the reflected optical signals into corresponding electrical signals of the optical signals by a stand-alone optical interrogator communicatively coupled to the console or an integrated optical interrogator integrated into the console. The optical signal-related operations also include conveying the input optical signals from the optical interrogator to a number of FBG sensors along a length of an optical-fiber stylet, as well as conveying the reflected optical signals from the number of FBG sensors back to the optical interrogator with the optical-fiber stylet disposed in a lumen of the medical device. The third processing operation includes processing the corresponding electrical signals of the optical signals with the processor into distance and orientation information with respect to the predefined target or area. The third displaying operation includes displaying an iconographic representation of a medical device on the display screen.

In some embodiments, the method further includes an adjusting operation in response to the optical signals. The adjusting operation includes adjusting the distance and orientation of the activated ultrasonic transducers with respect to the predefined target or area when the medical device is brought into proximity of the ultrasound probe. The adjusting operation establishes an image plane by the activated ultrasonic transducers perpendicular or parallel to a medical-device plane including the medical device for accessing the predefined target or area with the medical device.

In some embodiments, the method further includes an adjusting operation in response to an orientation of a blood vessel as the predefined target. The adjusting operation includes adjusting the distance and orientation of the activated ultrasonic transducers with respect to the orientation of the blood vessel. The adjusting operation establishes an image plane by the activated ultrasonic transducers perpendicular or parallel to the blood vessel.

In some embodiments, the establishing of the image plane is perpendicular to the medical-device plane upon approach of the medical device and parallel to the medical-device plane upon insertion of the medical device. The image plane includes a blood vessel as the predefined target or area and the medical-device plane includes a needle as the medical device.

In some embodiments, the activating operation includes activating an approximately linear subset of ultrasonic transducers of a 2-D array of ultrasonic transducers.

In some embodiments, the activating operation includes activating a subset of the ultrasonic transducers up to all the ultrasonic transducers in a movable linear array of ultrasonic transducers.

In some embodiments, the method further includes a data-providing operation and a fourth processing operation. The data providing operation includes providing positional-tracking data to the console from an accelerometer, a gyroscope, a magnetometer, or a combination thereof of the ultrasound probe. The fourth processing operation includes processing the positional-tracking data with the processor for the adjusting operation.

In some embodiments, the method further includes a maintaining operation. The maintaining operation includes maintaining the distance and the orientation of the activated ultrasonic transducers with respect to the predefined target or area when the ultrasound probe is inadvertently moved with respect to the predefined target or area.

These and other features of the concepts provided herein will become more apparent to those of skill in the art in view of the accompanying drawings and following description, which describe particular embodiments of such concepts in greater detail.

DRAWINGS

FIG. 21 illustrates the activated ultrasonic transducers of the array of ultrasonic transducers of the ultrasound probe perpendicular to the medical-device plane of the magnetized medical device in accordance with some embodiments.

FIG. 22 illustrates the activated ultrasonic transducers of the array of ultrasonic transducers of the ultrasound probe perpendicular to the medical-device plane of the magnetized medical device after yawing the medical device and dynamically adjusting the activated ultrasonic transducers in accordance with some embodiments.

FIG. 23 illustrates the activated ultrasonic transducers of the array of ultrasonic transducers of the ultrasound probe perpendicular to the medical-device plane of the magnetized medical device after yawing the medical device and dynamically adjusting the activated ultrasonic transducers in accordance with some embodiments.

DESCRIPTION

Figure 1:
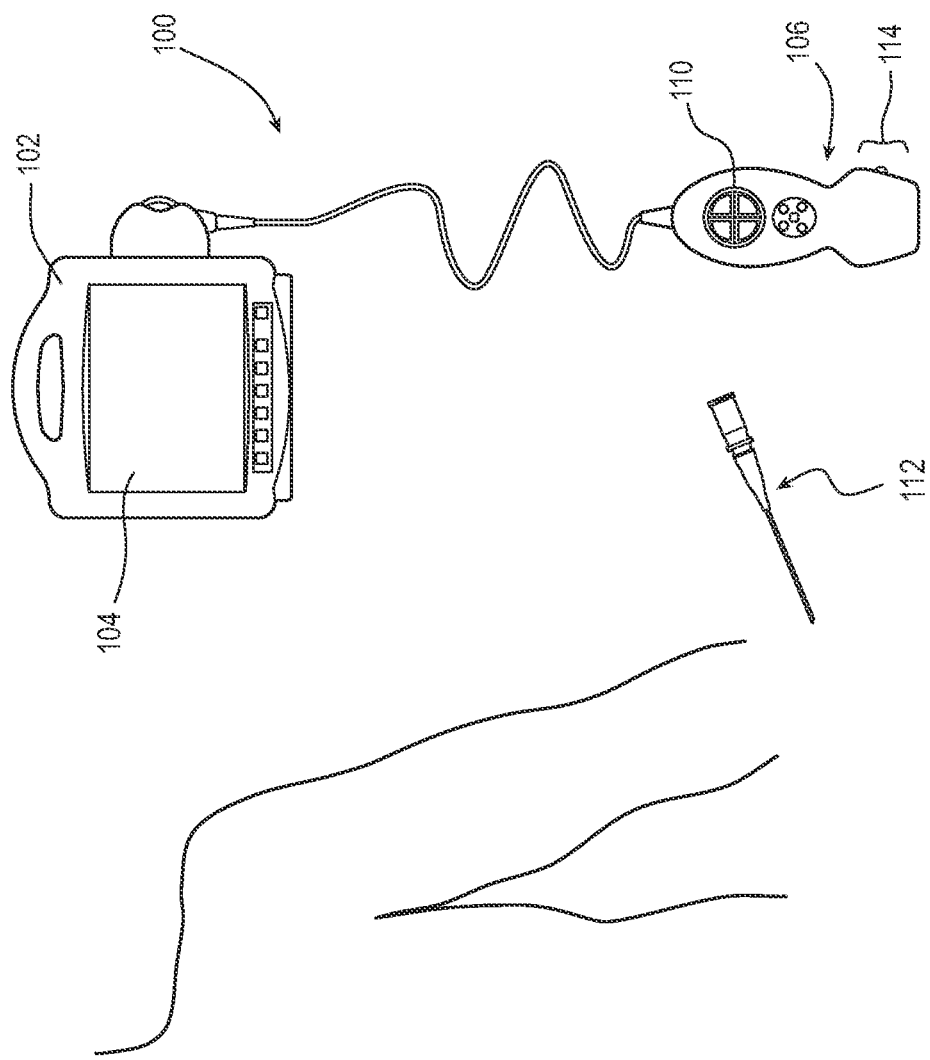
FIG. 1 illustrates an ultrasound-imaging system and a patient in accordance with some embodiments.
Figure 1:
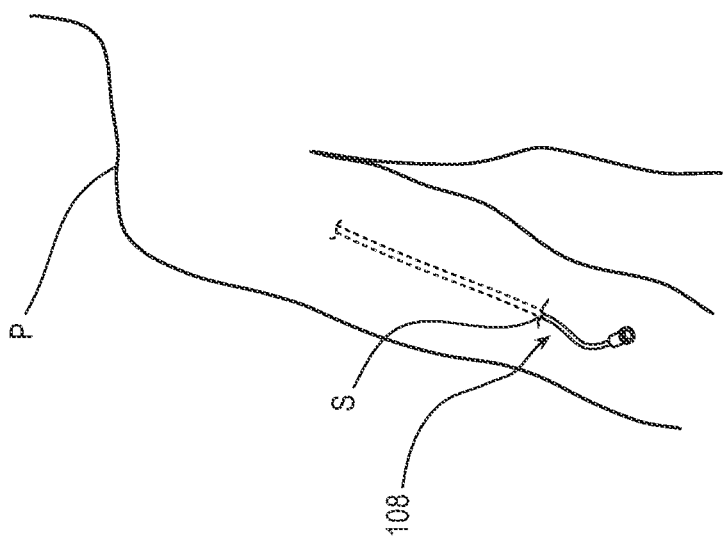

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, ultrasound-imaging systems and methods thereof are needed that can dynamically adjust the image plane to facilitate guiding interventional instruments to targets in at least the human body. Disclosed herein are dynamically adjusting ultrasound-imaging systems and methods thereof.

Ultrasound-Imaging Systems

Figure 2:
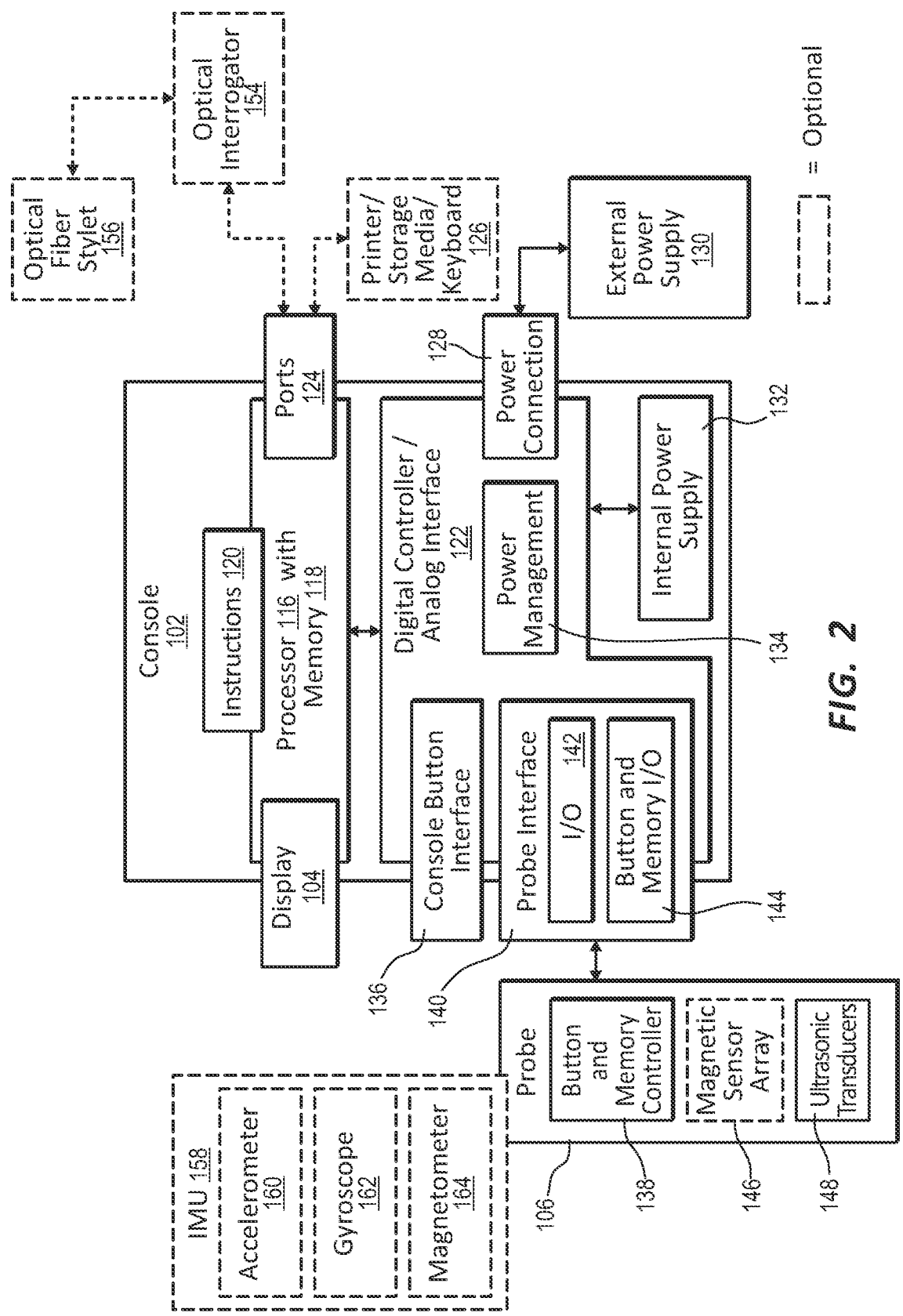
FIG. 2 illustrates a block diagram of the ultrasound-imaging system in accordance with some embodiments.
Figure 3B:
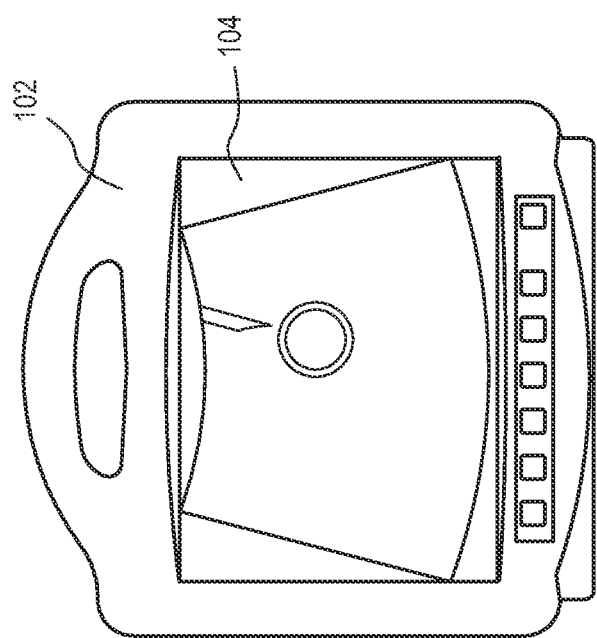
FIG. 3B illustrates an ultrasound image of the blood vessel of FIG. 3A on a display screen of the ultrasound-imaging system in accordance with some embodiments.
Figure 3A:
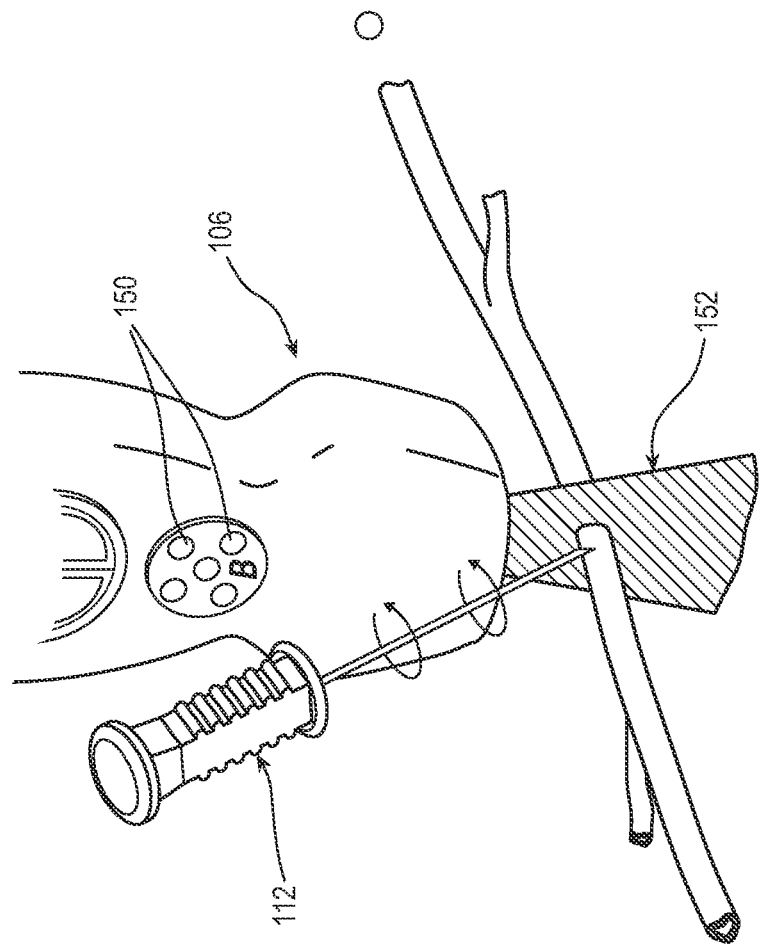
FIG. 3A illustrates an ultrasound probe of the ultrasound-imaging system imaging a blood vessel in accordance with some embodiments.

FIG. 1 illustrates an ultrasound-imaging system 100, a needle 112, and a patient P in accordance with some embodiments. FIG. 2 illustrates a block diagram of the ultrasound-imaging system 100 in accordance with some embodiments. FIG. 3A illustrates an ultrasound probe 106 of the ultrasound-imaging system 100 imaging a blood vessel of the patient P prior to accessing the blood vessel in accordance with some embodiments. FIG. 3B illustrates an ultrasound image of the blood vessel of FIG. 3A on a display screen 104 of the ultrasound-imaging system 100 with an iconographic representation of the needle 112 in accordance with some embodiments.

As shown, the ultrasound-imaging system 100 includes a console 102, the display screen 104, and the ultrasound probe 106. The ultrasound-imaging system 100 is useful for imaging a target such as a blood vessel or an organ within a body of the patient P prior to a percutaneous puncture with the needle 112 for inserting the needle 112 or another medical device into the target and accessing the target. Indeed, the ultrasound-imaging system 100 is shown in FIG. 1 in a general relationship to the patient P during an ultrasound-based medical procedure to place a catheter 108 into the vasculature of the patient P through a skin insertion site S created by a percutaneous puncture with the needle 112. It should be appreciated that the ultrasound-imaging system 100 can be useful in a variety of ultrasound-based medical procedures other than catheterization. For example, the percutaneous puncture with the needle 112 can be performed to biopsy tissue of an organ of the patient P.

The console 102 houses a variety of components of the ultrasound-imaging system 100, and it is appreciated the console 102 can take any of a variety of forms. A processor 116 and memory 118 such as random-access memory ("RAM") or non-volatile memory (e.g., electrically erasable programmable read-only memory ["EEPROM"]) is included in the console 102 for controlling functions of the ultrasound-imaging system 100, as well as executing various logic operations or algorithms during operation of the ultrasound-imaging system 100 in accordance executable instructions 120 therefor stored in the memory 118 for execution by the processor 116. For example, the console 102 is configured to instantiate by way of the instructions 120 one or more processes for dynamically adjusting a distance of activated ultrasonic transducers 149 from a predefined target (e.g., blood vessel) or area, an orientation of the activated ultrasonic transducers 149 to the predefined target or area, or both the distance and the orientation of the activated ultrasonic transducers 149 with respect to the predefined target or area, as well as process electrical signals from the ultrasound probe 106 into ultrasound images. Dynamically adjusting the activated ultrasonic transducers 149 uses ultrasound-imaging data, magnetic-field data, shape-sensing data, or a combination thereof received by the console 102 for activating certain ultrasonic transducers of a 2-D array of the ultrasonic transducers 148 or moving those already activated in a linear array of the ultrasonic transducers 148. A digital controller/analog interface 122 is also included with the console 102 and is in communication with both the processor 116 and other system components to govern interfacing between the ultrasound probe 106 and other system components set forth herein.

The ultrasound-imaging system 100 further includes ports 124 for connection with additional components such as optional components 126 including a printer, storage media, keyboard, etc. The ports 124 can be universal serial bus ("USB") ports, though other types of ports can be used for this connection or any other connections shown or described herein. A power connection 128 is included with the console 102 to enable operable connection to an external power supply 130. An internal power supply 132 (e.g., a battery) can also be employed either with or exclusive of the external power supply 130. Power management circuitry 134 is included with the digital controller/analog interface 122 of the console 102 to regulate power use and distribution.

Optionally, a stand-alone optical interrogator 154 can be communicatively coupled to the console 102 by way of one of the ports 124. Alternatively, the console 102 can include an integrated optical interrogator integrated into the console 102. Such an optical interrogator is configured to emit input optical signals into a companion optical-fiber stylet 156 for shape sensing with the ultrasound-imaging system 100, which optical-fiber stylet 156, in turn, is configured to be inserted into a lumen of a medical device such as the needle 112 and convey the input optical signals from the optical interrogator 154 to a number of FBG sensors along a length of the optical-fiber stylet 156. The optical interrogator 154 is also configured to receive reflected optical signals conveyed by the optical-fiber stylet 156 reflected from the number of FBG sensors, the reflected optical signals indicative of a shape of the optical-fiber stylet 156. The optical interrogator 154 is also configured to convert the reflected optical signals into corresponding electrical signals for processing by the console 102 into distance and orientation information with respect to the target for dynamically adjusting a distance of the activated ultrasonic transducers 149, an orientation of the activated ultrasonic transducers 149, or both the distance and the orientation of the activated ultrasonic transducers 149 with respect to the target or the medical device when it is brought into proximity of the target. For example, the distance and orientation of the activated ultrasonic transducers 149 can be adjusted with respect to a blood vessel as the target. Indeed, an image plane can be established by the activated ultrasonic transducers 149 being perpendicular or parallel to the blood vessel in accordance with an orientation of the blood vessel. In another example, when a medical device such as the needle 112 is brought into proximity of the ultrasound probe 106, an image plane can be established by the activated ultrasonic transducers 149 being perpendicular to a medical-device plane including the medical device as shown in FIGS. 11-13 and 21-23 or parallel to the medical-device plane including the medical device for accessing the target with the medical device. The image plane can be perpendicular to the medical-device plane upon approach of the medical device and parallel to the medical-device plane upon insertion of the medical device (e.g., percutaneous puncture with the needle 112). The distance and orientation information can also be used for displaying an iconographic representation of the medical device on the display.

The display screen 104 is integrated into the console 102 to provide a GUI and display information for a clinician during such as one-or-more ultrasound images of the target or the patient P attained by the ultrasound probe 106. In addition, the ultrasound-imaging system 100 enables the distance and orientation of a magnetized medical device such as the needle 112 to be superimposed in real-time atop an ultrasound image of the target, thus enabling a clinician to accurately guide the magnetized medical device to the intended target. Notwithstanding the foregoing, the display screen 104 can alternatively be separate from the console 102 and communicatively coupled thereto. A console button interface 136 and control buttons 110 (see FIG. 1) included on the ultrasound probe 106 can be used to immediately call up a desired mode to the display screen 104 by the clinician for assistance in an ultrasound-based medical procedure. In some embodiments, the display screen 104 is an LCD device.

The ultrasound probe 106 is employed in connection with ultrasound-based visualization of a target such as a blood vessel (see FIG. 3A) in preparation for inserting the needle 112 or another medical device into the target. Such visualization gives real-time ultrasound guidance and assists in reducing complications typically associated with such insertion, including inadvertent arterial puncture, hematoma, pneumothorax, etc. As described in more detail below, the ultrasound probe 106 is configured to provide to the console 102 electrical signals corresponding to both the ultrasound-imaging data, the magnetic-field data, the shape-sensing data, or a combination thereof for the real-time ultrasound guidance.

Figure 4:
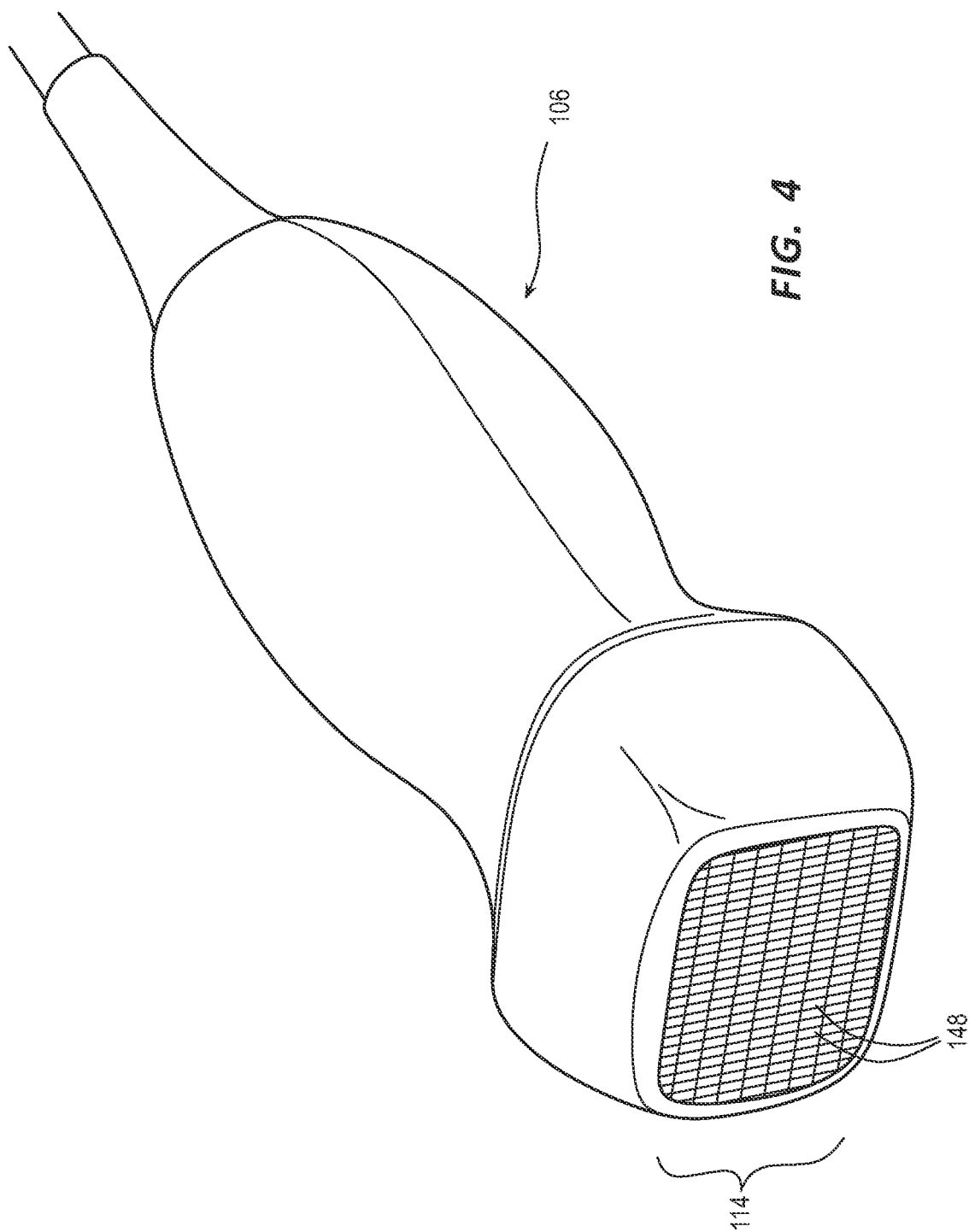
FIG. 4 illustrates the ultrasound probe of the ultrasound-imaging system configured as a 2-D ultrasound probe in accordance with some embodiments.
Figure 14:
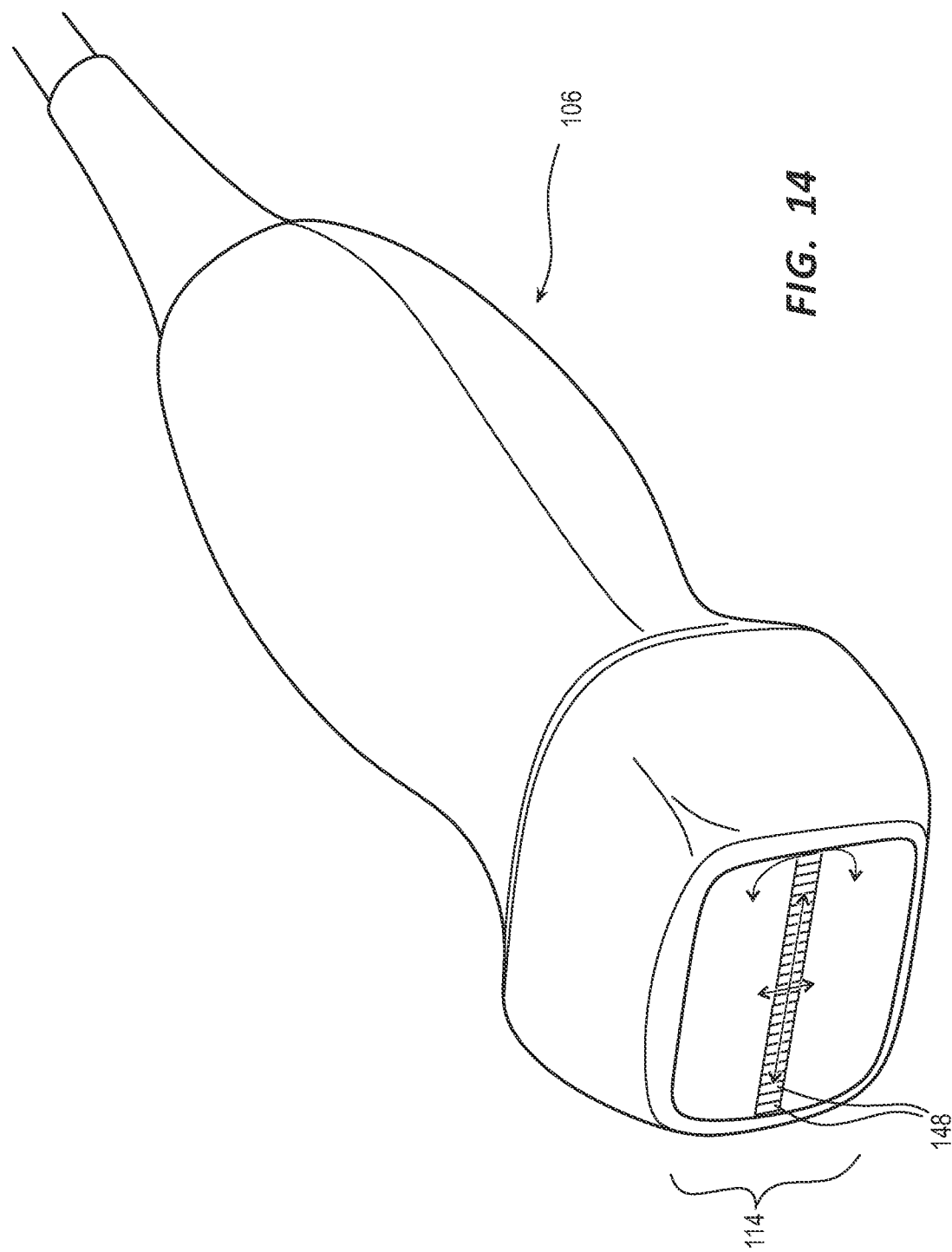
FIG. 14 illustrates the ultrasound probe of the ultrasound-imaging system configured as a linear ultrasound probe in accordance with some embodiments.

FIG. 4 illustrates the ultrasound probe 106 of the ultrasound-imaging system 100 configured as a 2-D ultrasound probe in accordance with some embodiments. FIG. 14 illustrates the ultrasound probe 106 of the ultrasound-imaging system 100 configured as a linear ultrasound probe in accordance with some embodiments.

The ultrasound probe 106 includes a probe head 114 that houses a mounted and moveable (e.g., translatable or rotatable along a central axis) linear array of the ultrasonic transducers 148 or a 2-D array of the ultrasonic transducers 148, wherein the ultrasonic transducers 148 are piezoelectric transducers or capacitive micromachined ultrasonic transducers ("CMUTs"). When the ultrasound probe 106 is configured with the 2-D array of the ultrasonic transducers 148, a subset of the ultrasonic transducers 148 is linearly activated as needed for ultrasound imaging in accordance with ultrasound-imaging data, magnetic-field data, shape-sensing data, or a combination thereof to maintain the target in an image plane or switch to a different image plane (e.g., from perpendicular to a medical-device plane to parallel to the medical-device plane) including the target. (See, for example, the activated ultrasonic transducers 149 of FIG. 5A, 7A, 10A, 12, or 13.) When the ultrasound probe 106 is configured with the moveable linear array of the ultrasonic transducers 148, the ultrasonic transducers 148 already activated for ultrasound imaging (e.g., a subset of the ultrasonic transducers 148 up to all the ultrasonic transducers 148) are moved together on the moveable linear array as needed for ultrasound imaging in accordance with ultrasound-imaging data, magnetic-field data, shape-sensing data, or a combination thereof to maintain the target in an image plane established by the activated ultrasonic transducers 149 or switch to a different image plane including the target. (See, for example, the activated ultrasonic transducers 149 of FIG. 15A, 17A, 20A, 22, or 23.)

The probe head 114 is configured for placement against skin of the patient P proximate a prospective needle-insertion site where the activated ultrasonic transducers 149 in the probe head 114 can generate and emit the generated ultrasound signals into the patient P in a number of pulses, receive reflected ultrasound signals or ultrasound echoes from the patient P by way of reflection of the generated ultrasonic pulses by the body of the patient P, and convert the reflected ultrasound signals into corresponding electrical signals for processing into ultrasound images by the console 102 to which the ultrasound probe 106 is communicatively coupled. In this way, a clinician can employ the ultrasound-imaging system 100 to determine a suitable insertion site and establish vascular access with the needle 112 or another medical device.

The ultrasound probe 106 further includes the control buttons 110 for controlling certain aspects of the ultrasound-imaging system 100 during an ultrasound-based medical procedure, thus eliminating the need for the clinician to reach out of a sterile field around the patient P to control the ultrasound-imaging system 100. For example, a control button of the control buttons 110 can be configured to select or lock onto the target (e.g., a blood vessel, an organ, etc.) when pressed for visualization of the target in preparation for inserting the needle 112 or another medical device into the target. Such a control button can also be configured to deselect the target, which is useful whether the target was selected by the control button or another means such as by holding the ultrasound probe 106 stationary over the target to select the target, issuing a voice command to select the target, or the like.

FIG. 2 shows that the ultrasound probe 106 further includes a button and memory controller 138 for governing button and ultrasound-probe operation. The button-and-memory controller 138 can include non-volatile memory (e.g., EEPROM). The button-and-memory controller 138 is in operable communication with a probe interface 140 of the console 102, which includes an input/output ("I/O") component 142 for interfacing with the ultrasonic transducers 148 and a button and memory I/O component 144 for interfacing with the button-and-memory controller 138.

Also as seen in FIGS. 2 and 3A, the ultrasound probe 106 can include a magnetic-sensor array 146 for detecting a magnetized medical device such as the needle 112 during ultrasound-based medical procedures. The magnetic-sensor array 146 includes a number of magnetic sensors 150 embedded within or included on a housing of the ultrasound probe 106. The magnetic sensors 150 are configured to detect a magnetic field or a disturbance in a magnetic field as magnetic signals associated with the magnetized medical device when it is in proximity to the magnetic-sensor array 146. The magnetic sensors 150 are also configured to convert the magnetic signals from the magnetized medical device (e.g., the needle 112) into electrical signals for the console 102 to process into distance and orientation information for the magnetized medical device with respect to the predefined target, as well as for display of an iconographic representation of the magnetized medical device on the display screen 104. (See the magnetic field B of the needle 112 in FIG. 3A.) Thus, the magnetic-sensor array 146 enables the ultrasound-imaging system 100 to track the needle 112 or the like.

Though configured here as magnetic sensors, it is appreciated that the magnetic sensors 150 can be sensors of other types and configurations. Also, though they are described herein as included with the ultrasound probe 106, the magnetic sensors 150 of the magnetic-sensor array 146 can be included in a component separate from the ultrasound probe 106 such as a sleeve into which the ultrasound probe 106 is inserted or even a separate handheld device. The magnetic sensors 150 can be disposed in an annular configuration about the probe head 114 of the ultrasound probe 106, though it is appreciated that the magnetic sensors 150 can be arranged in other configurations, such as in an arched, planar, or semi-circular arrangement.

Each magnetic sensor of the magnetic sensors 150 includes three orthogonal sensor coils for enabling detection of a magnetic field in three spatial dimensions. Such 3-dimensional ("3-D") magnetic sensors can be purchased, for example, from Honeywell Sensing and Control of Morristown, NJ. Further, the magnetic sensors 150 are configured as Hall-effect sensors, though other types of magnetic sensors could be employed. Further, instead of 3-D sensors, a plurality of 1-dimensional ("1-D") magnetic sensors can be included and arranged as desired to achieve 1-, 2-, or 3-D detection capability.

Five magnetic sensors for the magnetic sensors 150 are included in the magnetic-sensor array 146 so as to enable detection of a magnetized medical device such as the needle 112 in three spatial dimensions (e.g., X, Y, Z coordinate space), as well as the pitch and yaw orientation of the magnetized medical device itself. Detection of the magnetized medical device in accordance with the foregoing when the magnetized medical device is brought into proximity of the ultrasound probe 106 allows for dynamically adjusting a distance of the activated ultrasonic transducers 149, an orientation of the activated ultrasonic transducers 149, or both the distance and the orientation of the activated ultrasonic transducers 149 with respect to the target or the magnetized medical device. For example, the distance and orientation of the activated ultrasonic transducers 149 can be adjusted with respect to a blood vessel as the target. Indeed, an image plane can be established by the activated ultrasonic transducers 149 being perpendicular or parallel to the blood vessel in accordance with an orientation of the blood vessel. In another example, as shown among FIGS. 11-13 and 21-23, when the magnetized medical device is brought into proximity of the ultrasound probe 106, an image plane can be established by the activated ultrasonic transducers 149 being perpendicular to a medical-device plane including the magnetized medical device for accessing the target with the magnetized medical device. While not shown, the image plane can also be established by the activated ultrasonic transducers 149 being parallel to the medical-device plane including the magnetized medical device for accessing the target with the magnetized medical device such as after insertion of the medical device into the patient. Note that in some embodiments, orthogonal sensing components of two or more of the magnetic sensors 150 enable the pitch and yaw attitude of the magnetized medical device to be determined, which enables tracking with relatively high accuracy. In other embodiments, fewer than five or more than five magnetic sensors of the magnetic sensors 150 can be employed in the magnetic-sensor array 146. More generally, it is appreciated that the number, size, type, and placement of the magnetic sensors 150 of the magnetic-sensor array 146 can vary from what is explicitly shown here.

As shown in FIG. 2, the ultrasound probe 106 can further include an inertial measurement unit ("IMU") 158 or any one or more components thereof for inertial measurement selected from an accelerometer 160, a gyroscope 162, and a magnetometer 164 configured to provide positional-tracking data of the ultrasound probe 106 to the console 102 for stabilization of an image plane. The processor 116 is further configured to execute the instructions 120 for processing the positional-tracking data for adjusting the distance of the activated ultrasonic transducers 149 from the target, the orientation of the activated ultrasonic transducers 149 to the target, or both the distance and the orientation of the activated ultrasonic transducers 149 with respect to the target to maintain the distance and the orientation of the activated ultrasonic transducers 149 with respect to the target when the ultrasound probe 106 is inadvertently moved with respect to the target.

It is appreciated that a medical device of a magnetizable material enables the medical device (e.g., the needle 112) to be magnetized by a magnetizer, if not already magnetized, and tracked by the ultrasound-imaging system 100 when the magnetized medical device is brought into proximity of the magnetic sensors 150 of the magnetic-sensor array 146 or inserted into the body of the patient P during an ultrasound-based medical procedure. Such magnetic-based tracking of the magnetized medical device assists the clinician in placing a distal tip thereof in a desired location, such as in a lumen of a blood vessel, by superimposing a simulated needle image representing the real-time distance and orientation of the needle 112 over an ultrasound image of the body of the patient P being accessed by the magnetized medical device. Such a medical device can be stainless steel such as SS 304 stainless steel; however, other suitable needle materials that are capable of being magnetized can be employed. So configured, the needle 112 or the like can produce a magnetic field or create a magnetic disturbance in a magnetic field detectable as magnetic signals by the magnetic-sensor array 146 of the ultrasound probe 106 so as to enable the distance and orientation of the magnetized medical device to be tracked by the ultrasound-imaging system 100 for dynamically adjusting the distance of the activated ultrasonic transducers 149, an orientation of the activated ultrasonic transducers 149, or both the distance and the orientation of the activated ultrasonic transducers 149 with respect to the magnetized medical device.

During operation of the ultrasound-imaging system 100, the probe head 114 of the ultrasound probe 106 is placed against skin of the patient P. An ultrasound beam 152 is produced so as to ultrasonically image a portion of a target such as a blood vessel beneath a surface of the skin of the patient P. (See FIG. 3A.) The ultrasonic image of the blood vessel can be depicted and stabilized on the display screen 104 of the ultrasound-imaging system 100 as shown in FIG. 3B despite inadvertent movements of the ultrasound probe 106. Indeed, this is shown among FIGS. 5A, 5B, 7A, 7B, 8A, 8B, 10A, and 10B for the ultrasound probe 106 configured with the 2-D array of the ultrasonic transducers 148 and FIGS. 15A, 15B, 17A, 17B, 18A, 18B, 20A, and 20B for the ultrasound probe 106 configured with the moveable linear array of the ultrasonic transducers 148.

Figure 7A:
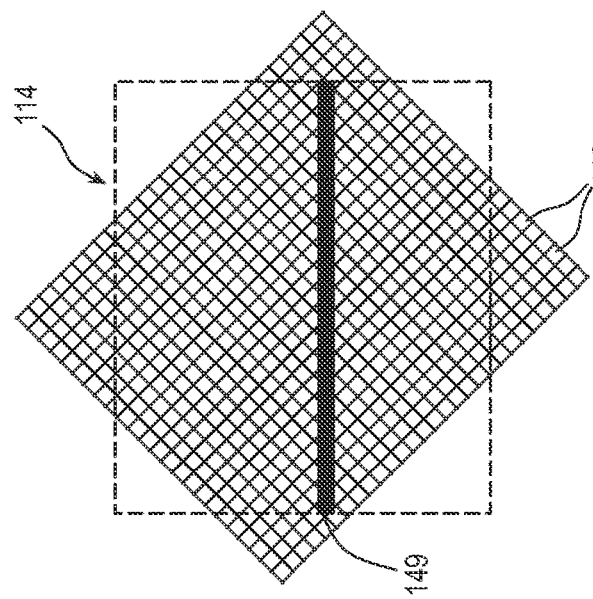
FIG. 7A illustrates the activated ultrasonic transducers of the ultrasound probe of FIG. 5A upon rotating the ultrasound probe with dynamic adjusting of the activated ultrasonic transducers in accordance with some embodiments.
Figure 7B:
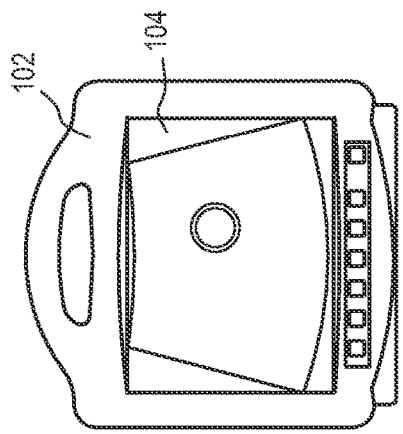
FIG. 7B illustrates the ultrasound image of the blood vessel of FIG. 3A obtained with the activated ultrasonic transducers of FIG. 7A on the display screen of the ultrasound-imaging system in accordance with some embodiments.
Figure 5A:
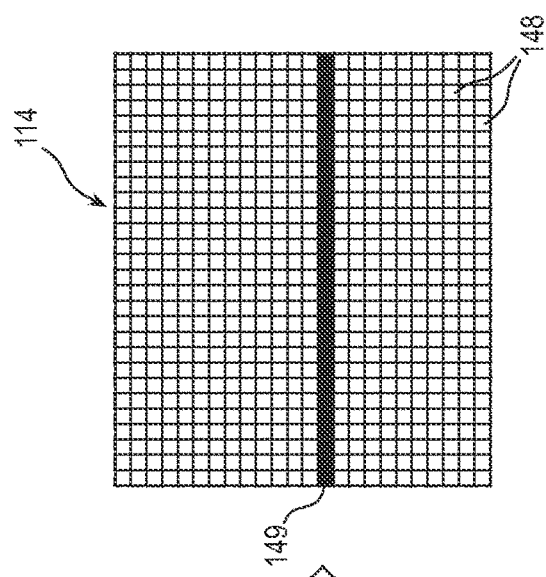
FIG. 5A illustrates activated ultrasonic transducers of an array of ultrasonic transducers of the ultrasound probe in accordance with some embodiments.
Figure 5B:
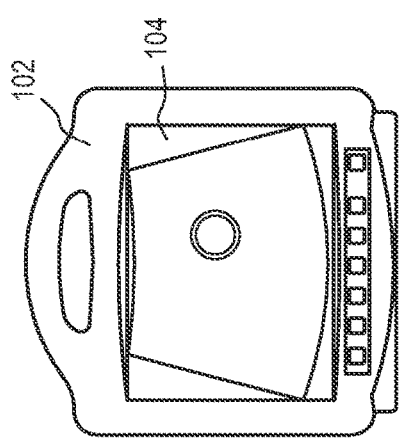
FIG. 5B illustrates the ultrasound image of the blood vessel of FIG. 3A obtained with the activated ultrasonic transducers of FIG. 5A on the display screen of the ultrasound-imaging system in accordance with some embodiments.
Figure 6A:
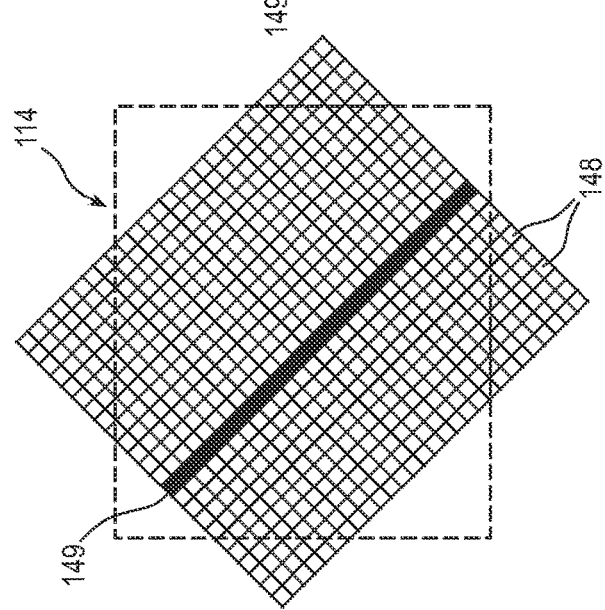
FIG. 6A illustrates the activated ultrasonic transducers of the ultrasound probe of FIG. 5A upon rotating the ultrasound probe without dynamic adjusting of the activated ultrasonic transducers in accordance with some embodiments.
Figure 6B:
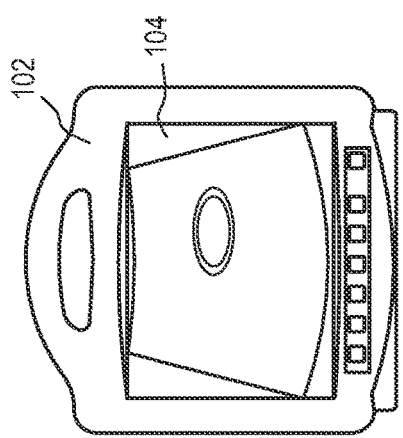
FIG. 6B illustrates the ultrasound image of the blood vessel of FIG. 3A obtained with the activated ultrasonic transducers of FIG. 6A on the display screen of the ultrasound-imaging system in accordance with some embodiments.
Figure 15A:
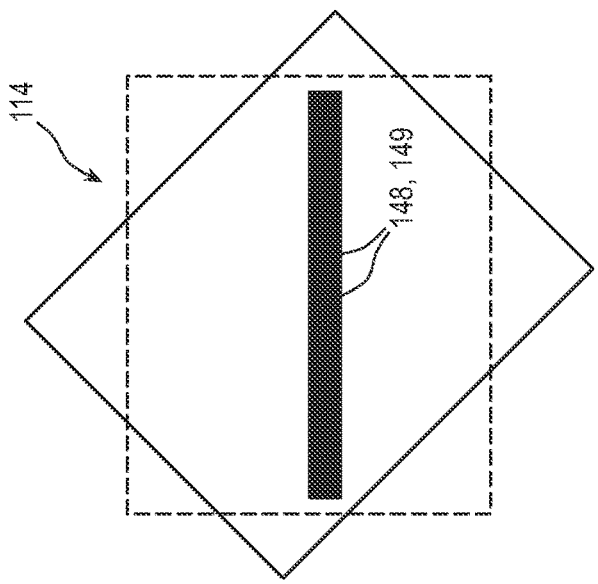
FIG. 15A illustrates activated ultrasonic transducers of an array of ultrasonic transducers of the ultrasound probe in accordance with some embodiments.
Figure 15B:
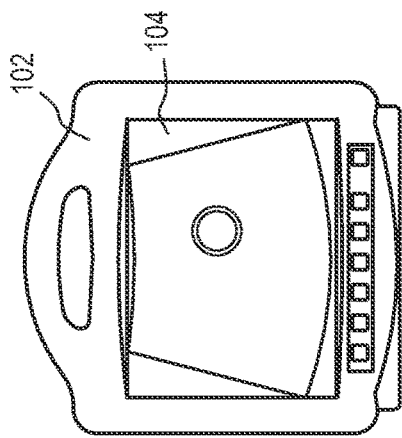
FIG. 15B illustrates the ultrasound image of the blood vessel of FIG. 3A obtained with the activated ultrasonic transducers of FIG. 15A on the display screen of the ultrasound-imaging system in accordance with some embodiments.
Figure 16A:
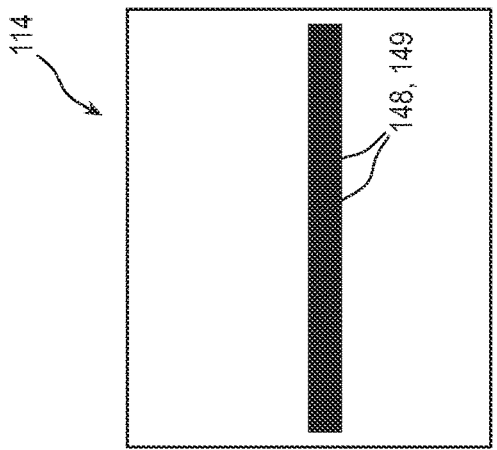
FIG. 16A illustrates the activated ultrasonic transducers of the ultrasound probe of FIG. 15A upon rotating the ultrasound probe without dynamic adjusting of the activated ultrasonic transducers in accordance with some embodiments.
Figure 16B:
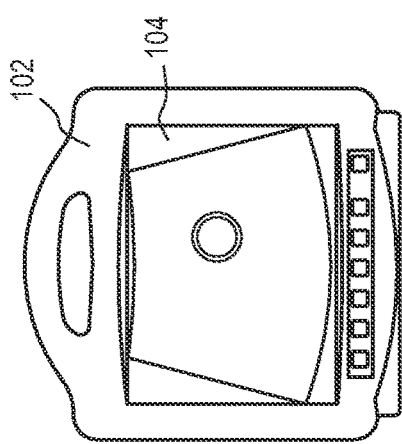
FIG. 16B illustrates the ultrasound image of the blood vessel of FIG. 3A obtained with the activated ultrasonic transducers of FIG. 16A on the display screen of the ultrasound-imaging system in accordance with some embodiments.
Figure 17A:
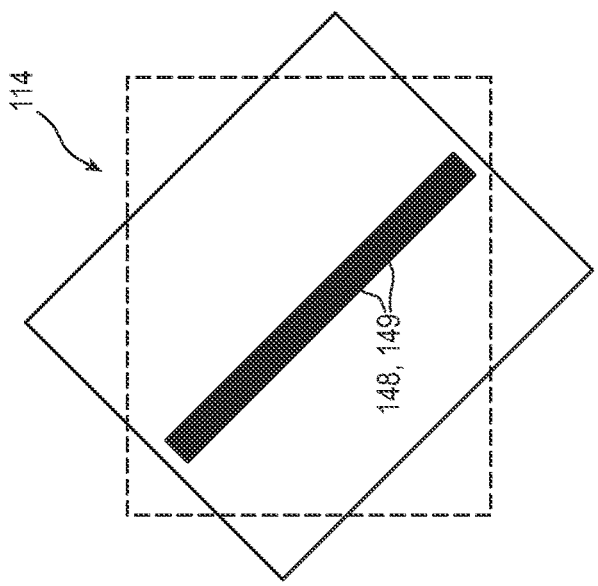
FIG. 17A illustrates the activated ultrasonic transducers of the ultrasound probe of FIG. 15A upon rotating the ultrasound probe with dynamic adjusting of the activated ultrasonic transducers in accordance with some embodiments.
Figure 17B:
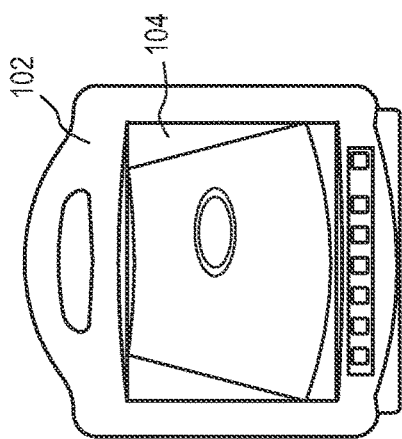
FIG. 17B illustrates the ultrasound image of the blood vessel of FIG. 3A obtained with the activated ultrasonic transducers of FIG. 17A on the display screen of the ultrasound-imaging system in accordance with some embodiments.

FIGS. 5A and 5B illustrate the activated ultrasonic transducers 149 of the 2-D array of the ultrasonic transducers 148 of the ultrasound probe 106 in accordance with some embodiments. FIGS. 15A and 15B illustrate the activated ultrasonic transducers 149 of the moveable linear array of the ultrasonic transducers 148 of the ultrasound probe 106 in accordance with some embodiments. As shown in FIG. 7A, upon rotating the ultrasound probe 106 as might occur with an inadvertent movement of the ultrasound probe 106, dynamic adjustment of the activated ultrasonic transducers 149 occurs to maintain the target in the image plane. Such dynamic adjustment includes deactivating certain ultrasonic transducers and activating certain other ultrasonic transducers to maintain a distance and orientation of the activated ultrasonic transducers 149 to the target, which stabilizes the ultrasound image as shown in FIG. 7B. (Compare FIG. 7B with 5B.) Without such dynamic adjustment as shown by FIG. 6A, the distance and orientation of the activated ultrasonic transducers 149 to the target is not maintained, which results in a different ultrasound image as shown in FIG. 6B. (Compare FIG. 6B with 5B.) Likewise, as shown in FIG. 17A, upon rotating the ultrasound probe 106 as might occur with an inadvertent movement of the ultrasound probe 106, dynamic adjustment of the activated ultrasonic transducers 149 occurs to maintain the target in the image plane. Such dynamic adjustment includes automatically rotating the moveable linear array of the ultrasonic transducers 148 (within the probe head 114) to maintain a distance and orientation of the activated ultrasonic transducers 149 to the target, which stabilizes the ultrasound image as shown in FIG. 17B. (Compare FIG. 17B with 15B.) Without such dynamic adjustment as shown by FIG. 16A, the distance and orientation of the activated ultrasonic transducers 149 to the target is not maintained, which results in a different ultrasound image as shown in FIG. 16B. (Compare FIG. 16B with 15B.)

Figure 10A:
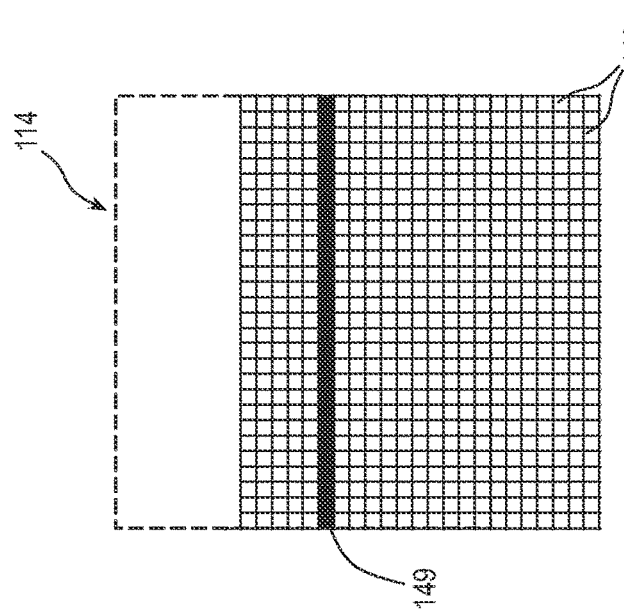
FIG. 10A illustrates the activated ultrasonic transducers of the ultrasound probe of FIG. 10A upon translating the ultrasound probe with dynamic adjusting of the activated ultrasonic transducers in accordance with some embodiments.
Figure 10B:
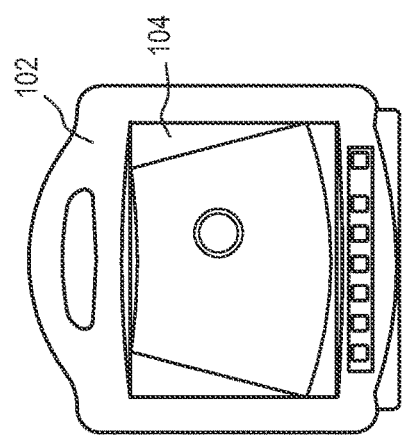
FIG. 10B illustrates the ultrasound image of the blood vessel of FIG. 3A obtained with the activated ultrasonic transducers of FIG. 10A on the display screen of the ultrasound-imaging system in accordance with some embodiments.
Figure 8A:
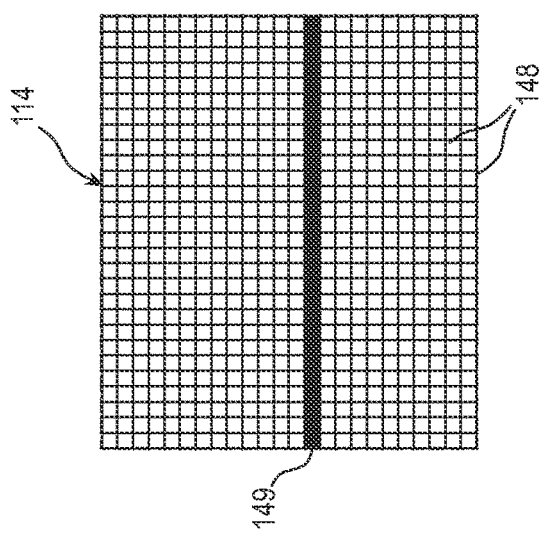
FIG. 8A illustrates the activated ultrasonic transducers of the array of ultrasonic transducers of the ultrasound probe in accordance with some embodiments.
Figure 8B:
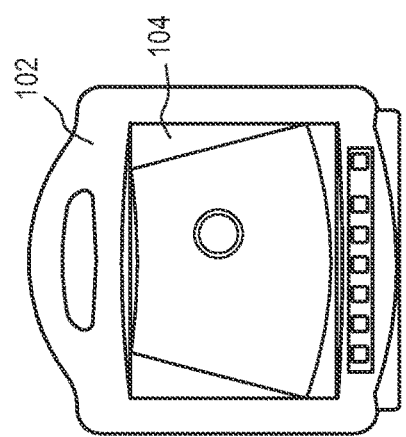
FIG. 8B illustrates the ultrasound image of the blood vessel of FIG. 3A obtained with the activated ultrasonic transducers of FIG. 8A on the display screen of the ultrasound-imaging system in accordance with some embodiments.
Figure 9A:
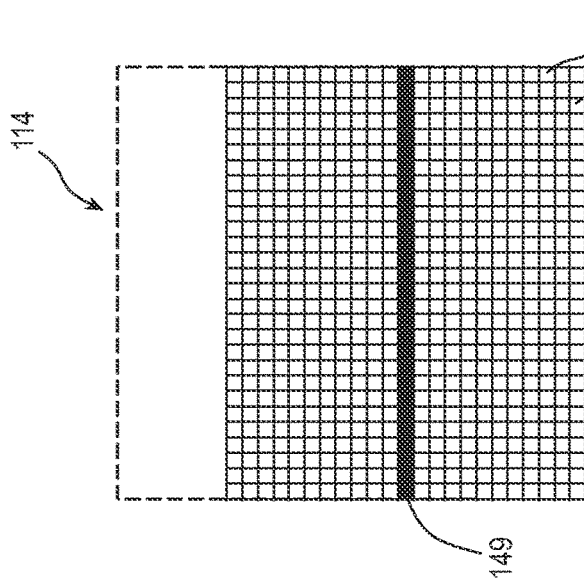
FIG. 9A illustrates the activated ultrasonic transducers of the ultrasound probe of FIG. 8A upon translating the ultrasound probe without dynamic adjusting of the activated ultrasonic transducers in accordance with some embodiments.
Figure 9B:
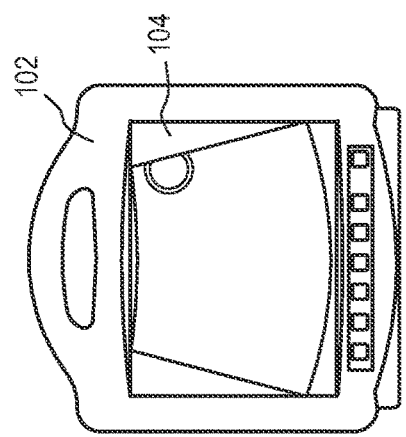
FIG. 9B illustrates the ultrasound image of the blood vessel of FIG. 3A obtained with the activated ultrasonic transducers of FIG. 9A on the display screen of the ultrasound-imaging system in accordance with some embodiments.
Figure 13:
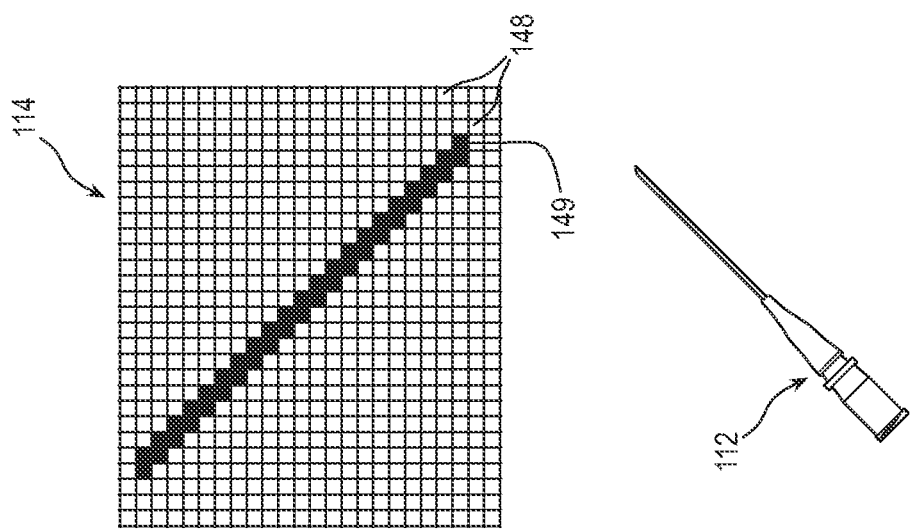
FIG. 13 illustrates the activated ultrasonic transducers of the array of ultrasonic transducers of the ultrasound probe perpendicular to the medical-device plane of the magnetized medical device after yawing the medical device and dynamically adjusting the activated ultrasonic transducers in accordance with some embodiments.
Figure 11:
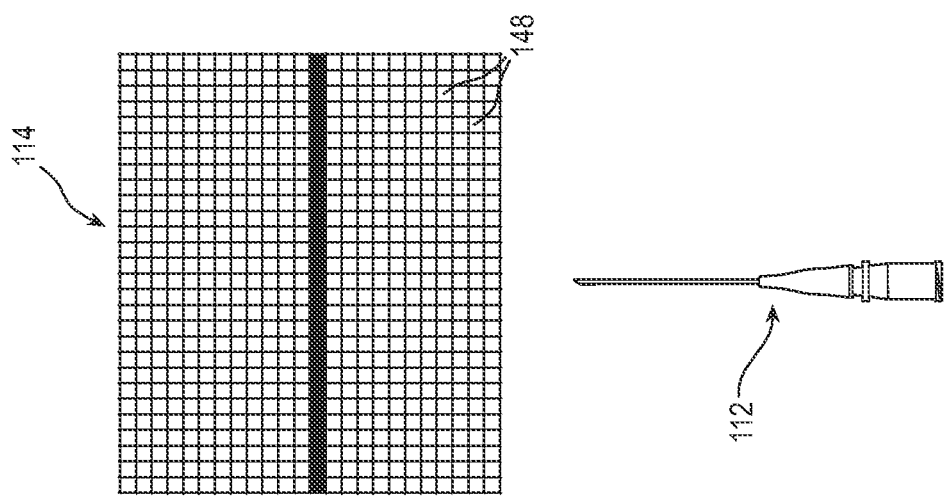
FIG. 11 illustrates the activated ultrasonic transducers of the array of ultrasonic transducers of the ultrasound probe perpendicular to a medical-device plane of a magnetized medical device in accordance with some embodiments.
Figure 12:
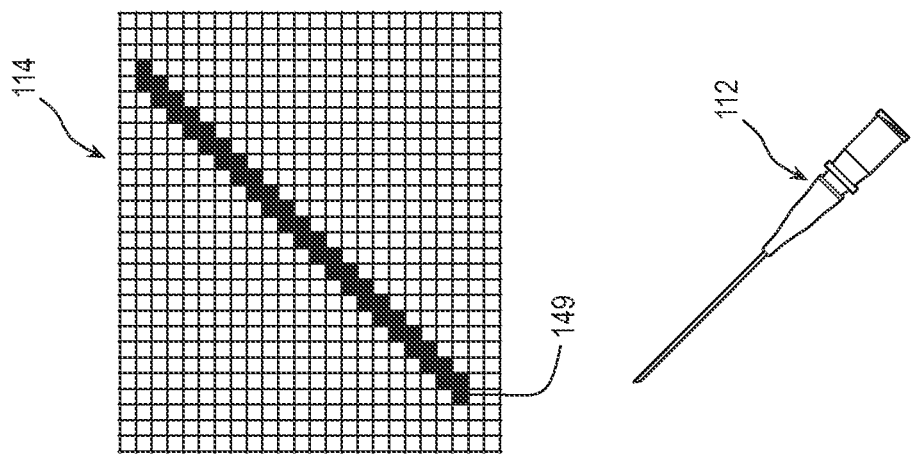
FIG. 12 illustrates the activated ultrasonic transducers of the array of ultrasonic transducers of the ultrasound probe perpendicular to the medical-device plane of the magnetized medical device after yawing the medical device and dynamically adjusting the activated ultrasonic transducers in accordance with some embodiments.
Figure 18A:
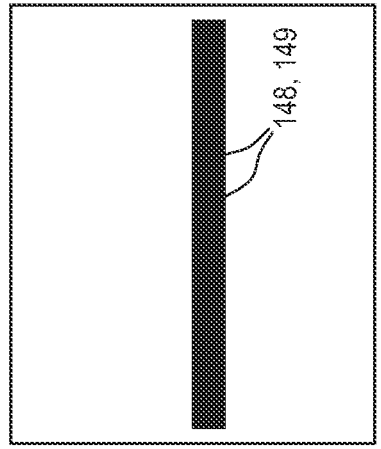
FIG. 18A illustrates the activated ultrasonic transducers of the array of ultrasonic transducers of the ultrasound probe in accordance with some embodiments.
Figure 18B:
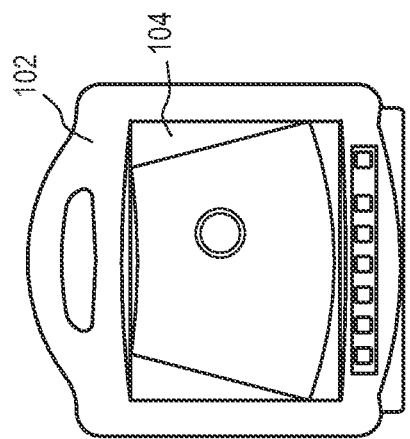
FIG. 18B illustrates the ultrasound image of the blood vessel of FIG. 3A obtained with the activated ultrasonic transducers of FIG. 18A on the display screen of the ultrasound-imaging system in accordance with some embodiments.
Figure 19A:
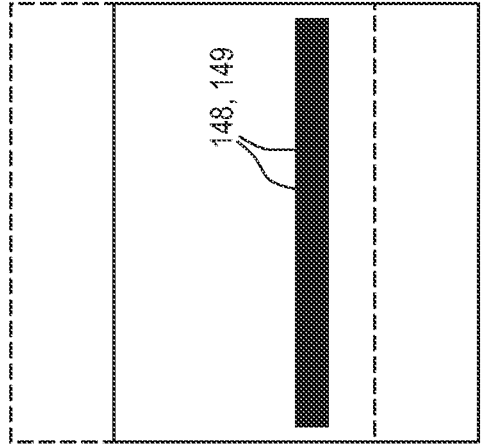
FIG. 19A illustrates the activated ultrasonic transducers of the ultrasound probe of FIG. 18A upon translating the ultrasound probe without dynamic adjusting of the activated ultrasonic transducers in accordance with some embodiments.
Figure 19B:
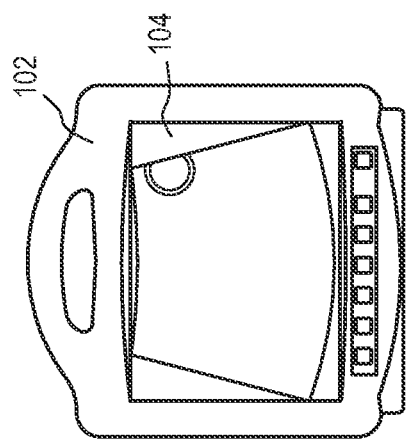
FIG. 19B illustrates the ultrasound image of the blood vessel of FIG. 3A obtained with the activated ultrasonic transducers of FIG. 19A on the display screen of the ultrasound-imaging system in accordance with some embodiments.
Figure 20A:
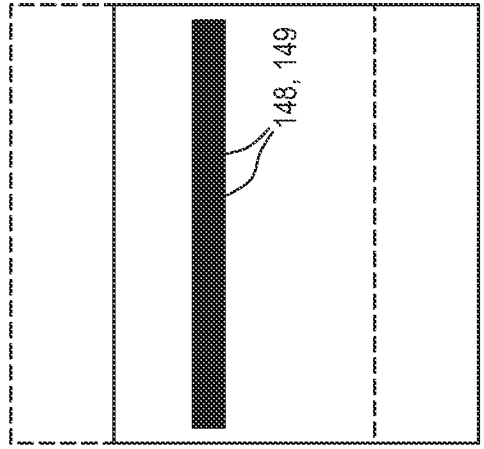
FIG. 20A illustrates the activated ultrasonic transducers of the ultrasound probe of FIG. 20A upon translating the ultrasound probe with dynamic adjusting of the activated ultrasonic transducers in accordance with some embodiments.
Figure 20B:
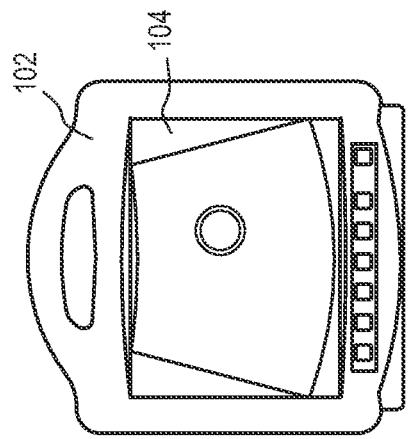
FIG. 20B illustrates the ultrasound image of the blood vessel of FIG. 3A obtained with the activated ultrasonic transducers of FIG. 20A on the display screen of the ultrasound-imaging system in accordance with some embodiments.

FIGS. 8A and 8B illustrate the activated ultrasonic transducers 149 of the 2-D array of the ultrasonic transducers 148 of the ultrasound probe 106 in accordance with some embodiments. FIGS. 18A and 18B illustrate the activated ultrasonic transducers 149 of the moveable linear array of the ultrasonic transducers 148 of the ultrasound probe 106 in accordance with some embodiments. As shown in FIG. 10A, upon translating the ultrasound probe 106 as might occur with an inadvertence movement of the ultrasound probe 106, dynamic adjustment of the activated ultrasonic transducers 149 occurs to maintain the target in the image plane. Such dynamic adjustment includes deactivating certain ultrasonic transducers and activating certain other ultrasonic transducers to maintain a distance and orientation of the activated ultrasonic transducers 149 to the target, which stabilizes the ultrasound image as shown in FIG. 10B. (Compare FIG. 10B with 8B.) Without such dynamic adjustment as shown by FIG. 9A, the distance and orientation of the activated ultrasonic transducers 149 to the target is not maintained, which results in a different ultrasound image as shown in FIG. 9B. (Compare FIG. 9B with 8B.) Likewise, as shown in FIG. 20A, upon translating the ultrasound probe 106 as might occur with an inadvertent movement of the ultrasound probe 106, dynamic adjustment of the activated ultrasonic transducers 149 occurs to maintain the target in the image plane. Such dynamic adjustment includes automatically translating the moveable linear array of the ultrasonic transducers 148 (within the probe head 114) to maintain a distance and orientation of the activated ultrasonic transducers 149 to the target, which stabilizes the ultrasound image as shown in FIG. 20B. (Compare FIG. 20B with 18B.) Without such dynamic adjustment as shown by FIG. 19A, the distance and orientation of the activated ultrasonic transducers 149 to the target is not maintained, which results in a different ultrasound image as shown in FIG. 19B. (Compare FIG. 19B with 18B.)

The ultrasound-imaging system 100 is configured to detect the distance and orientation of a medical device by way of the magnetic sensors 150 or shape-sensing optical-fiber stylet 156. By way of example, the magnetic-sensor array 146 of the ultrasound probe 106 is configured to detect a magnetic field of the magnetized medical device or a disturbance in a magnetic field due to the magnetized magnetic device. Each magnetic sensor of the magnetic sensors 150 in the magnetic-sensor array 146 is configured to spatially detect the needle 112 in 3-dimensional space. (See FIG. 3A.) Thus, during operation of the ultrasound-imaging system 100, magnetic field strength data of the medical device's magnetic field sensed by each magnetic sensor of the magnetic sensors 150 is forwarded to the processor 116 of the console 102, which computes in real-time the distance and orientation of the magnetized medical device useful for dynamically adjusting a distance of the activated ultrasonic transducers 149, an orientation of the activated ultrasonic transducers 149, or both the distance and the orientation of the activated ultrasonic transducers 149 with respect to the magnetized medical device. Again, the distance and orientation of the magnetized medical device is also for graphical display on the display screen 104.

The distance or orientation of any point along an entire length of the magnetized medical device in a coordinate space with respect to the magnetic-sensor array 146 can be determined by the ultrasound-imaging system 100 using the magnetic-field strength data sensed by the magnetic sensors 150. Moreover, a pitch and yaw of the needle 112 can also be determined. Suitable circuitry of the ultrasound probe 106, the console 102, or other components of the ultrasound-imaging system 100 can provide the calculations necessary for such distance or orientation. In some embodiments, the needle 112 can be tracked using the teachings of one or more patents of U.S. Pat. Nos. 5,775,322; 5,879,297; 6,129,668; 6,216,028; and 6,263,230, each of which is incorporated by reference in its entirety into this application.

The distance and orientation information determined by the ultrasound-imaging system 100, together with an entire length of the magnetized medical device, as known by or input into the ultrasound-imaging system 100, enables the ultrasound-imaging system 100 to accurately determine the distance and orientation of the entire length of the magnetized medical device, including a distal tip thereof, with respect to the magnetic-sensor array 146. This, in turn, enables the ultrasound-imaging system 100 to superimpose an image of the needle 112 on an ultrasound image produced by the ultrasound beam 152 of the ultrasound probe 106 on the display screen 104, as well as dynamically adjusting the activated ultrasonic transducers 149. For example, the ultrasound image depicted on the display screen 104 can include depiction of the surface of the skin of the patient P and a subcutaneous blood vessel thereunder to be accessed by the needle 112, as well as a depiction of the magnetized medical device as detected by the ultrasound-imaging system 100 and its orientation to the vessel. The ultrasound image corresponds to an image acquired by the ultrasound beam 152 of the ultrasound probe 106. It should be appreciated that only a portion of an entire length of the magnetized medical device is magnetized and, thus, tracked by the ultrasound-imaging system 100.

Note that further details regarding structure and operation of the ultrasound-imaging system 100 can be found in U.S. Pat. No. 9,456,766, titled "Apparatus for Use with Needle Insertion Guidance System," which is incorporated by reference in its entirety into this application.

Methods

Methods of the foregoing ultrasound-imaging systems include methods implemented in the ultrasound-imaging systems. For example, a method of the ultrasound-imaging system 100 includes a non-transitory CRM (e.g., EEPROM) having the instructions 120 stored thereon that cause the ultrasound-imaging system 100 to perform a set of operations for ultrasound imaging when the instructions 120 are executed by the processor 116 of the console 102. Such a method includes an activating operation, an adjusting operation, a first processing operation, and a first displaying operation.

The activating operation includes activating the ultrasonic transducers of the array of the ultrasonic transducers 148 of the ultrasound probe 106 communicatively coupled to the console 102. With the activating operation, the ultrasonic transducers 148 emit generated ultrasound signals into the patient P, receive reflected ultrasound signals from the patient P, and convert the reflected ultrasound signals into corresponding electrical signals for processing into ultrasound images. The activating operation can include activating an approximately linear subset of the ultrasonic transducers 148 of a 2-D array of the ultrasonic transducers 148. Alternatively, the activating operation can include activating a subset of the ultrasonic transducers 148 up to all the ultrasonic transducers 148 in the movable linear array of the ultrasonic transducers 148.

The adjusting operation includes dynamically adjusting a distance of the activated ultrasonic transducers 149 from a predefined target or area, an orientation of the activated ultrasonic transducers 149 to the predefined target or area, or both the distance and the orientation of the activated ultrasonic transducers 149 with respect to the predefined target or area. For example, the adjusting operation can be in response to an orientation of a blood vessel as the predefined target. The adjusting operation includes adjusting the distance and orientation of the activated ultrasonic transducers 149 with respect to the orientation of the blood vessel so as to establish an image plane by the activated ultrasonic transducers 149 perpendicular or parallel to the blood vessel.

The first processing operation includes processing the corresponding electrical signals of the ultrasound signals into the ultrasound images.

The first displaying operation includes displaying on the display screen 104 communicatively coupled to the console 102 the GUI including the ultrasound images.

As to magnetic signal-related operations, the method can include a converting operation, a second processing operation, and a second displaying operation. The converting operation includes converting magnetic signals from a magnetized medical device (e.g., the needle 112) with the magnetic-sensor array 146 of the ultrasound probe 106 into corresponding electrical signals. The second processing operation includes processing the corresponding electrical signals of the magnetic signals with the processor 116 into distance and orientation information with respect to the predefined target or area. The second displaying operation includes displaying an iconographic representation of the medical device on the display screen 104.

The method further includes an adjusting operation in response to the magnetic signals. The adjusting operation includes adjusting the distance and orientation of the activated ultrasonic transducers 149 with respect to the predefined target or area when the medical device is brought into proximity of the ultrasound probe 106. The adjusting operation establishes an image plane by the activated ultrasonic transducers 149 perpendicular or parallel to the medical-device plane including the medical device for accessing the predefined target or area with the medical device. The establishing of the image plane can be perpendicular to the medical-device plane upon approach of the medical device and parallel to the medical-device plane upon insertion of the medical device. The image plane can include a blood vessel as the predefined target or area and the medical-device plane can include the needle 112 as the medical device.

As to optical signal-related operations, the method can include a number of optical signal-related operations, as well as a third processing operation and a third displaying operation. The optical signal-related operations include emitting input optical signals, receiving reflected optical signals, and converting the reflected optical signals into corresponding electrical signals of the optical signals by the optical interrogator 154. The optical signal-related operations also include conveying the input optical signals from the optical interrogator 154 to the number of FBG sensors along the length of the optical-fiber stylet 156, as well as conveying the reflected optical signals from the number of FBG sensors back to the optical interrogator 154 with the optical-fiber stylet 156 disposed in a lumen of the medical device. The third processing operation includes processing the corresponding electrical signals of the optical signals with the processor 116 into distance and orientation information with respect to the predefined target or area. The third displaying operation includes displaying an iconographic representation of a medical device on the display screen 104.

The method further includes an adjusting operation in response to the optical signals. The adjusting operation includes adjusting the distance and orientation of the activated ultrasonic transducers 149 with respect to the predefined target or area when the medical device is brought into proximity of the ultrasound probe 106. The adjusting operation establishes an image plane by the activated ultrasonic transducers 149 perpendicular or parallel to the medical-device plane including the medical device for accessing the predefined target or area with the medical device. Again, the establishing of the image plane is perpendicular to the medical-device plane upon approach of the medical device and parallel to the medical-device plane upon insertion of the medical device. The image plane includes a blood vessel as the predefined target or area and the medical-device plane includes the needle 112 as the medical device.

The method can further include a data-providing operation and a fourth processing operation. The data-providing operation includes providing positional-tracking data to the console 102 from the accelerometer 160, the gyroscope 162, the magnetometer 164, or a combination thereof of the ultrasound probe 106. The fourth processing operation includes processing the positional-tracking data with the processor 116 for the adjusting operation.

The method can further include a maintaining operation. The maintaining operation includes maintaining the distance and the orientation of the activated ultrasonic transducers 149 with respect to the predefined target or area when the ultrasound probe 106 is inadvertently moved with respect to the predefined target or area.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound-imaging system, comprising:
an ultrasound probe including an array of ultrasonic transducers, activated ultrasonic transducers of the array of ultrasonic transducers configured to emit generated ultrasound signals into a patient, receive reflected ultrasound signals from the patient, and convert the reflected ultrasound signals into corresponding electrical signals for processing into ultrasound images;
a console configured to communicate with the ultrasound probe, the console including memory with executable instructions and a processor configured to execute the instructions for:
dynamically adjusting a distance and an orientation of the activated ultrasonic transducers with respect to a predefined target or area within a body in response to a medical device brought into proximity of the ultrasound probe before accessing the predefined target or area with the medical device such that an image plane established by the activated ultrasonic transducers is perpendicular or parallel to either the medical device or the predefined target or area; and
processing the corresponding electrical signals of the ultrasound signals into the ultrasound images; and
a display screen configured to communicate with the console, the display screen configured to display a graphical user interface ("GUI") including the ultrasound images.

2. The ultrasound-imaging system of claim 1, the ultrasound probe further comprising: an array of magnetic sensors configured to convert magnetic signals from the medical device, when magnetized, into corresponding electrical signals of the magnetic signals for processing by the processor into distance and orientation information with respect to the predefined target or area for display of an iconographic representation of the medical device on the display screen.

3. The ultrasound-imaging system of claim 2, wherein the distance and orientation of the activated ultrasonic transducers is adjusted with respect to the predefined target or area when the medical device is brought into proximity of the ultrasound probe, the image plane established by the activated ultrasonic transducers being perpendicular or parallel to a medical-device plane including the medical device for accessing the predefined target or area with the medical device.

4. The ultrasound-imaging system of claim 3, wherein the image plane includes a blood vessel as the predefined target and the medical device includes a needle, the image plane being perpendicular to the medical-device plane upon approach of the needle to the ultrasound probe and parallel to the medical-device plane upon a percutaneous puncture with the needle.

5. The ultrasound-imaging system of claim 2, wherein the distance and orientation of the activated ultrasonic transducers is adjusted with respect to a blood vessel as the predefined target, the image plane established by the activated ultrasonic transducers being perpendicular or parallel to the blood vessel in accordance with an orientation of the blood vessel.

6. The ultrasound-imaging system of claim 1, further comprising:
a stand-alone optical interrogator communicatively coupled to the console or an integrated optical interrogator integrated into the console, the optical interrogator configured to emit input optical signals, receive reflected optical signals, and convert the reflected optical signals into corresponding electrical signals of the reflected optical signals for processing by the processor into distance and orientation information with respect to the predefined target or area for display of an iconographic representation of the medical device on the display; and
an optical-fiber stylet configured to convey the input optical signals from the optical interrogator to a number of fiber Bragg grating ("FBG") sensors along a length of the optical-fiber stylet and the reflected optical signals from the number of FBG sensors back to the optical interrogator, the optical-fiber stylet configured to be disposed in a lumen of the medical device.

7. The ultrasound-imaging system of claim 6, wherein the distance and orientation of the activated ultrasonic transducers is adjusted with respect to the predefined target or area when the medical device is brought into proximity of the ultrasound probe, the image plane established by the activated ultrasonic transducers being perpendicular or parallel to a medical-device plane including the medical device for accessing the predefined target or area with the medical device.

8. The ultrasound-imaging system of claim 6, wherein the distance and orientation of the activated ultrasonic transducers is adjusted with respect to a blood vessel as the predefined target, the image plane established by the activated ultrasonic transducers being perpendicular or parallel to the blood vessel in accordance with an orientation of the blood vessel.

9. The ultrasound-imaging system of claim 1, wherein the array of ultrasonic transducers is a two-dimensional array of ultrasonic transducers, the activated ultrasonic transducers being an approximately linear subset of ultrasonic transducers of the two-dimensional array of ultrasonic transducers activated by the console at any given time.

10. The ultrasound-imaging system of claim 9, the ultrasound probe further comprising an accelerometer, a gyroscope, a magnetometer, or a combination thereof configured to provide positional-tracking data to the console, the processor further configured to execute the instructions for processing the positional-tracking data for adjusting the distance of the activated ultrasonic transducers from the predefined target or area, the orientation of the activated ultrasonic transducers to the predefined target or area, or both the distance and the orientation of the activated ultrasonic transducers with respect to the predefined target or area.

11. The ultrasound-imaging system of claim 9, wherein the distance and the orientation of the activated ultrasonic transducers is maintained with respect to the predefined target or area when the ultrasound probe is inadvertently moved with respect to the predefined target or area.

12. The ultrasound-imaging system of claim 1, wherein the array of ultrasonic transducers is a movable linear array of ultrasonic transducers, the activated ultrasonic transducers being a subset of the ultrasonic transducers up to all the ultrasonic transducers in the movable linear array of ultrasonic transducers activated by the console at any given time.

13. A method of an ultrasound-imaging system including a non-transitory computer-readable medium ("CRM") having executable instructions that cause the ultrasound-imaging system to perform a set of operations for ultrasound imaging when the instructions are executed by a processor of a console of the ultrasound-imaging system, the method comprising:
activating ultrasonic transducers of an array of ultrasonic transducers of an ultrasound probe communicatively coupled to the console, whereby the ultrasonic transducers emit generated ultrasound signals into a patient, receive reflected ultrasound signals from the patient, and convert the reflected ultrasound signals into corresponding electrical signals for processing into ultrasound images;
dynamically adjusting a distance and an orientation of activated ultrasonic transducers with respect to a predefined target or area within a body in response to a medical device brought into proximity of the ultrasound probe before accessing the predefined target or area with the medical device such that an image plane established by the activated ultrasonic transducers is perpendicular or parallel to either the medical device or the predefined target or area;
processing the corresponding electrical signals into the ultrasound images; and
displaying on a display screen communicatively coupled to the console a graphical user interface ("GUI") including the ultrasound images.

14. The method of claim 13, further comprising:
converting magnetic signals from the medical device, when magnetized, with an array of magnetic sensors of the ultrasound probe into corresponding electrical signals of the magnetic signals;
processing the corresponding electrical signals of the magnetic signals with the processor into distance and orientation information with respect to the predefined target or area; and
displaying an iconographic representation of the medical device on the display screen.

15. The method of claim 14, further comprising adjusting the distance and orientation of the activated ultrasonic transducers with respect to the predefined target or area when the medical device is brought into proximity of the ultrasound probe, thereby establishing the image plane by the activated ultrasonic transducers perpendicular or parallel to a medical-device plane including the medical device for accessing the predefined target or area with the medical device.

16. The method of claim 15, wherein establishing the image plane is perpendicular to the medical-device plane upon approach of the medical device to the ultrasound probe and parallel to the medical-device plane upon insertion of the medical device, the image plane including a blood vessel as the predefined target and the medical-device plane including a needle as the medical device.

17. The method of claim 14, further comprising adjusting the distance and orientation of the activated ultrasonic transducers with respect to an orientation of a blood vessel as the predefined target, thereby establishing the image plane by the activated ultrasonic transducers perpendicular or parallel to the blood vessel.

18. The method of claim 13, further comprising:
emitting input optical signals, receiving reflected optical signals, and converting the reflected optical signals into corresponding electrical signals of the reflected optical signals by a stand-alone optical interrogator communicatively coupled to the console or an integrated optical interrogator integrated into the console;
conveying the input optical signals from the optical interrogator to a number of fiber Bragg grating ("FBG") sensors along a length of an optical-fiber stylet and the reflected optical signals from the number of FBG sensors back to the optical interrogator with the optical-fiber stylet disposed in a lumen of the medical device;
processing the corresponding electrical signals of the optical signals with the processor into distance and orientation information with respect to the predefined target or area; and
displaying an iconographic representation of the medical device on the display screen.

19. The method of claim 18, further comprising adjusting the distance and orientation of the activated ultrasonic transducers with respect to the predefined target or area when the medical device is brought into proximity of the ultrasound probe, thereby establishing the image plane by the activated ultrasonic transducers perpendicular or parallel to a medical-device plane including the medical device for accessing the predefined target or area with the medical device.

20. The method of claim 18, further comprising adjusting the distance and orientation of the activated ultrasonic transducers with respect to an orientation of a blood vessel as the predefined target, thereby establishing the image plane by the activated ultrasonic transducers perpendicular or parallel to the blood vessel.

21. The method of claim 13, wherein activating the ultrasonic transducers of the array of ultrasonic transducers includes activating an approximately linear subset of ultrasonic transducers of a two-dimensional array of ultrasonic transducers.

22. The method of claim 21, further comprising:
providing positional-tracking data to the console from an accelerometer, a gyroscope, a magnetometer, or a combination thereof of the ultrasound probe; and
processing the positional-tracking data with the processor for adjusting the distance of the activated ultrasonic transducers from the predefined target or area, the orientation of the activated ultrasonic transducers to the predefined target or area, or both the distance and the orientation of the activated ultrasonic transducers with respect to the predefined target or area.

23. The method of claim 21, further comprising maintaining the distance and the orientation of the activated ultrasonic transducers with respect to the predefined target or area when the ultrasound probe is inadvertently moved with respect to the predefined target or area.

24. The method of claim 13, wherein the activating of the ultrasonic transducers of the array of ultrasonic transducers includes activating a subset of the ultrasonic transducers up to all the ultrasonic transducers in a movable linear array of ultrasonic transducers.

* * * * *